United States Patent
Atreya et al.

(10) Patent No.: US 9,243,036 B2
(45) Date of Patent: Jan. 26, 2016

(54) ANTI-MICROBIAL ACTIVITY OF SYNTHETIC PEPTIDES

(75) Inventors: Chintamani Atreya, Bethesda, MD (US); Shilpakala Sainath Rao, Derwood, MD (US); Krishna Mohan V. Ketha, Derwood, MD (US)

(73) Assignee: THE UNITED STATES OF AMERICA, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 14/421,428

(22) PCT Filed: Aug. 15, 2012

(86) PCT No.: PCT/US2012/050969
§ 371 (c)(1), (2), (4) Date: Feb. 12, 2015

(87) PCT Pub. No.: WO2014/028011
PCT Pub. Date: Feb. 20, 2014

(65) Prior Publication Data
US 2015/0322113 A1    Nov. 12, 2015

(51) Int. Cl.
*C07K 7/06* (2006.01)
*C07K 7/08* (2006.01)
*A61K 38/00* (2006.01)

(52) U.S. Cl.
CPC ... *C07K 7/08* (2013.01); *C07K 7/06* (2013.01); *A61K 38/00* (2013.01)

(58) Field of Classification Search
CPC ............ C07K 7/06; C07K 7/08; A61K 38/00
See application file for complete search history.

(56) References Cited

FOREIGN PATENT DOCUMENTS

WO    WO 02/070547 A1    9/2002
WO    WO 2005/090385    9/2005

OTHER PUBLICATIONS

Aoki et al., "Next Generation of Antimicrobial Peptides as Molecular Targeted Medicines," *Journal of Bioscience and bioengineering* 114(4):365-370 (Oct. 2012).
Da Silva and Machado, "Antimicrobial Peptides: Clinical Relevance and Therapeutic Implications," *Peptides* 36:308-314 (2012).
International Search Report from the parent PCT Application No. PCT/US2012/050969, 6 pages (mailed Sep. 20, 2012).
Jiang et al., "Effects of Net Charge and the Number of Positively Charged Residues on the Biological Activity of Amphipathic α-Helical Cationic Antimicrobial Peptides," *Biopolymers* 90(3): 369-383 (2008).
Jin-Jiang et al., "The Design and Construction of K11: A Novel α-Helical Antimicrobial Peptide," *International Journal of Microbiology* Article ID 764834, pp. 1-6 (2012).
Li et al., "Bactericidal Activity Against Meticillin-resistant *Staphylococcus aureus* of a Novel Eukaryotic Therapeutic Recombinant Antimicrobial Peptide," *International Journal of Antimicrobial Agents* 39(6):496-9 (Jun. 2012).
Min et al., "The Antimicrobial Activity of the Appetite Peptide Hormone Ghrelin," *Peptides* 36(2):151-156 (Aug. 2012).
Rao et al., "Antibacterial Activity of a Novel Peptide Derived from Phage-displayed Random Peptide Library," *51st Interscience Conference on Antimicrobial Agents and Chemotherapy* (Sep. 17-20, 2011)(Abstract).
Rao et al., "A Peptide Derived from Phage Display Library Exhibits Antibacterial Activity against *E. coli* and Pseudomonas aeruginosa," *PLOS* 8(2)(e56081):1-11 (Feb. 2013).
Written Opinion from the parent PCT Application No. PCT/US2012/050969, 6 pages (mailed Sep. 20, 2012).

*Primary Examiner* — Amber D Steele
(74) *Attorney, Agent, or Firm* — Klarquist Sparkman, LLP

(57) ABSTRACT

Isolated synthetic peptides are disclosed that have anti-microbial activity against *E. coli* and *P. aeruginosa*. These isolated peptides can be used as anti-viral agents. The use of these peptides to treat infections with *E. coli* and *P. aeruginosa* and viruses are disclosed. The disclosed peptides are also of use for treating a biofilm, such as a biofilm on a medical device.

10 Claims, 11 Drawing Sheets

SEQUENCE LISTING

<160> NUMBER OF SEQ ID NOS: 8

<210> SEQ ID NO 1
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is R or W
<220> FEATURE:
<221> NAME/KEY: MISC_FEATURE
<222> LOCATION: (2)..(2)
<223> OTHER INFORMATION: X is L, C or no amino acid
<220> FEATURE:
<221> NAME/KEY: MISC_FEATURE
<222> LOCATION: (5)..(5)
<223> OTHER INFORMATION: X is R or no amino acid
<220> FEATURE:
<221> NAME/KEY: MISC_FEATURE
<222> LOCATION: (6)..(6)
<223> OTHER INFORMATION: X is K, C or no amino acid
<220> FEATURE:
<221> NAME/KEY: MISC_FEATURE
<222> LOCATION: (7)..(7)
<223> OTHER INFORMATION: X is I or no amino acid
<220> FEATURE:
<221> NAME/KEY: MISC_FEATURE
<222> LOCATION: (8)..(8)
<223> OTHER INFORMATION: X is R or no amino acid
<220> FEATURE:
<221> NAME/KEY: MISC_FEATURE
<222> LOCATION: (9)..(9)
<223> OTHER INFORMATION: X is R, C or no amino acid
<220> FEATURE:
<221> NAME/KEY: MISC_FEATURE
<222> LOCATION: (10)..(10)
<223> OTHER INFORMATION: X is L or no amino acid
<220> FEATURE:
<221> NAME/KEY: MISC_FEATURE
<222> LOCATION: (11)..(11)
<223> OTHER INFORMATION: X is K or no amino acid
<220> FEATURE:
<221> NAME/KEY: MISC_FEATURE
<222> LOCATION: (12)..(12)
<223> OTHER INFORMATION: X is R or W

<400> SEQUENCE: 1

Xaa Xaa Leu Phe Xaa Xaa Xaa Xaa Xaa Xaa Xaa Xaa
1               5                   10

<210> SEQ ID NO 2
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is R or no amino acid
<220> FEATURE:
<221> NAME/KEY: MISC_FEATURE
<222> LOCATION: (2)..(2)
<223> OTHER INFORMATION: X is R, C, A, W or no amino acid
<220> FEATURE:
<221> NAME/KEY: MISC_FEATURE
<222> LOCATION: (3)..(3)
<223> OTHER INFORMATION: X is R, C, A, W or no amino acid
<220> FEATURE:
<221> NAME/KEY: MISC_FEATURE
<222> LOCATION: (4)..(4)
<223> OTHER INFORMATION: X is R or W
<220> FEATURE:

```
<221> NAME/KEY: MISC_FEATURE
<222> LOCATION: (5)..(5)
<223> OTHER INFORMATION: X is L, C or no amino acid
<220> FEATURE:
<221> NAME/KEY: MISC_FEATURE
<222> LOCATION: (8)..(8)
<223> OTHER INFORMATION: X is R or no amino acid
<220> FEATURE:
<221> NAME/KEY: MISC_FEATURE
<222> LOCATION: (9)..(9)
<223> OTHER INFORMATION: X is K, C or no amino acid
<220> FEATURE:
<221> NAME/KEY: MISC_FEATURE
<222> LOCATION: (10)..(10)
<223> OTHER INFORMATION: X is I or no amino acid
<220> FEATURE:
<221> NAME/KEY: MISC_FEATURE
<222> LOCATION: (11)..(11)
<223> OTHER INFORMATION: X is R or no amino acid
<220> FEATURE:
<221> NAME/KEY: MISC_FEATURE
<222> LOCATION: (12)..(12)
<223> OTHER INFORMATION: X is R, C or no amino acid
<220> FEATURE:
<221> NAME/KEY: MISC_FEATURE
<222> LOCATION: (13)..(13)
<223> OTHER INFORMATION: X is L or no amino acid
<220> FEATURE:
<221> NAME/KEY: MISC_FEATURE
<222> LOCATION: (14)..(14)
<223> OTHER INFORMATION: X is K or no amino acid
<220> FEATURE:
<221> NAME/KEY: MISC_FEATURE
<222> LOCATION: (15)..(15)
<223> OTHER INFORMATION: X is R or W
<220> FEATURE:
<221> NAME/KEY: MISC_FEATURE
<222> LOCATION: (16)..(16)
<223> OTHER INFORMATION: X is C, A, W or no amino acid
<220> FEATURE:
<221> NAME/KEY: MISC_FEATURE
<222> LOCATION: (17)..(17)
<223> OTHER INFORMATION: X is C, A, W or no amino acid

<400> SEQUENCE: 2

Xaa Xaa Xaa Xaa Xaa Leu Phe Xaa Xaa Xaa Xaa Xaa Xaa Xaa Xaa Xaa
1               5                   10                  15

Xaa Trp

<210> SEQ ID NO 3
<211> LENGTH: 12
<212> TYPE: PRT
<213> ORGANISM: Artificial Sequence
<220> FEATURE:
<223> OTHER INFORMATION: Synthetic peptide

<400> SEQUENCE: 3

Arg Leu Leu Phe Arg Lys Ile Arg Arg Leu Lys Arg
1               5                   10

<210> SEQ ID NO 4
<211> LENGTH: 12
<212> TYPE: PRT
<213> ORGANISM: Artificial Sequence
<220> FEATURE:
<223> OTHER INFORMATION: synthetic peptide

<400> SEQUENCE: 4

Ser Gly His Gln Leu Leu Leu Asn Lys Met Pro Asn
1               5                   10

<210> SEQ ID NO 5
```

```
<211> LENGTH: 12
<212> TYPE: PRT
<213> ORGANISM: Artificial Sequence
<220> FEATURE:
<223> OTHER INFORMATION: Synthetic peptide

<400> SEQUENCE: 5

Met Asp Met Arg Thr Thr Asp Ile Arg Asp Thr Ser
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Synthetic peptide

<400> SEQUENCE: 6

Arg Asn His Pro Ala Thr Leu Thr Gly Thr Gly Gly
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Synthetic peptide

<400> SEQUENCE: 7

Gly Ile Leu Ser Glu Leu Gly Lys Ala Leu Gly Gly
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Synthetic peptide

<400> SEQUENCE: 8

Gly Ala Pro Ala Leu Ser Thr Pro Pro Leu Ser Arg
1               5                   10
```

ANTI-MICROBIAL ACTIVITY OF SYNTHETIC PEPTIDES

CROSS REFERENCE TO RELATED APPLICATIONS

This is the U.S. National Stage of International Application No. PCT/US2012/050969, filed Aug. 15, 2012, which was published in English under PCT Article 21(2), which is incorporated by reference herein.

FIELD OF THE DISCLOSURE

This related to the field of anti-microbial and anti-viral agents, specifically to synthetic peptides that can be used to treat or prevent infection with specific types of bacteria and viruses.

BACKGROUND

Drug resistance among pathogenic bacteria is on the rise and antibiotics to combat these microbes are becoming limited. New anti-bacterial agents with novel mechanisms of action and biological targets need to be developed. Anti-Microbial Peptides (AMPs) are a new class of anti-microbial agents that has stimulated the interest of many investigators as a substitute for traditional antibiotics (Jenssen, H., Hamill, P., and Hancock, R. E. (2006) *Clin. Microbiol. Rev.* 19, 491-511). Most of the AMPs are components of innate immunity that evolved millions of years ago as primary defense to combat microbial challenge (Ganz, T. (2003) *Nat. Rev. Immunol.* 3, 710-720). Though human defensins and cathelicidins from higher vertebrates are the most studied AMPs, significant number of diverse AMPs from plants, vertebrates, and invertebrates are also receiving lots of attention (Yeaman, M. R. and Yount, N. Y. (2007) *Nat. Rev. Microbiol.* 5, 727-740; Yount, N. Y. and Yeaman, M. R. (2004) *Proc. Natl. Acad. Sci. U. S. A* 101, 7363-7368). AMPs have a positive net charge and interact with the negatively charged membranes, leading to destabilization and permeabilization of the cell membrane (Hancock, R. E. and Rozek, A. (2002) *FEMS Microbiol. Lett.* 206, 143-149; Wu, M., Maier, E., Benz, R., and Hancock, R. E. (1999) *Biochemistry* 38, 7235-7242; Zhang, L., Rozek, A., and Hancock, R. E. (2001) *J. Biol. Chem.* 276, 35714-35722).

Though the exact mode of action of the AMPs has not been fully understood, several models for the interaction of AMPs with membranes such as the "carpet model, "toroid pore" model and the "barrel-stave" model have been proposed (Yeaman, M. R. and Yount, N. Y. (2003) *Pharmacol. Rev.* 55, 27-55). The mechanism of action of AMPs against Gram-negative bacteria has been extensively studied (Falla, T. J., Karunaratne, D. N., and Hancock, R. E. (1996) *J. Biol. Chem.* 271, 19298-19303). Many of the anti-microbial peptides act by binding to the negatively charged lipopolysaccharide (LPS), thereby rendering the bacterial membrane permeable. Additional peptide molecules present outside the membrane gain entry into the cell and integrate into the cytoplasmic membrane resulting in cell death (Hancock, R. E., Falla, T., and Brown, M. (1995) *Adv. Microb. Physiol* 37, 135-175). However, some AMPs may act differently under different conditions (Park Y., and Hahm K. S. (2005) *J Biochem Mol Biol* 38, 507-516). A need remains for AMPs that can target specific types of bacteria.

SUMMARY OF THE DISCLOSURE

Isolated peptides are disclosed that have anti-microbial activity against *E. coli* and *P. aeruginosa*. These isolated peptides can be used as anti-viral agents. In some embodiments, the isolated peptide is 9 to 15 amino acids in length, and includes the amino acid sequence set forth as:

$X_1X_2LFX_3X_4X_5X_6X_7X_8X_9X_{10}$ (SEQ ID NO: 1)

wherein $X_1$ is R or W, $X_2$ is L, C or no amino acid; $X_3$ is R or no amino acid; $X_4$ is K, C or no amino acid; $X_5$ is I or no amino acid; $X_6$ is R or no amino acid; $X_7$ is R, C or no amino acid; $X_8$ is L or no amino acid; $X_9$ is K or no amino acid; and $X_{10}$ is R or W. The peptide has a hydrophobicity score of 40-60%, a net charge of +5 to +7, and has anti-microbial activity against *E. coli* and *P. aeruginosa*. In one specific non-limiting example, the antimicrobial peptide has the amino acid sequence set forth as RLLFRKIRRLKR (SEQ ID NO: 1, wherein $X_1$ is R; $X_2$ is L; $X_3$ is R; $X_4$ is K; $X_5$ is I; $X_6$ is R; $X_7$ is R; $X_8$ is L; and $X_9$ is K and $X_{10}$ is R, also set forth as SEQ ID NO: 3). Nucleic acids encoding these peptides, vectors including coding sequences for these peptides, and host cells transformed with these vectors are also disclosed, as are compositions including the peptides, nucleic acids, vectors and host cells. The peptides can be used in combination with other agents, such as other peptides, anti-bacterial agents and antiviral agents.

In some embodiments, methods are disclosed for treating or preventing an infection with *E. coli*, *P. aeruginosa*, or both, in a subject. These methods include administering to the subject a therapeutically effective amount of a composition including an anti-microbial peptide, nucleic acid encoding the anti-microbial peptide, or vector including the nucleic acid, thereby treating or preventing the infection with *E. coli*, *P. aeruginosa*, or both. In additional embodiments, methods are provided for treating or preventing a viral infection. These methods include administering to the subject a therapeutically effective amount of the composition including the anti-microbial peptide, nucleic acid encoding the anti-microbial peptide, or vector including the nucleic acid, thereby treating or preventing the viral infection.

In further embodiments, methods are provided for killing a bacterium, comprising contacting the bacterium with an effective amount of the anti-microbial peptide, thereby killing the bacterium, wherein the bacterium is *E. coli* or *P. aeruginosa*. In yet other embodiments, methods are disclosed for lysing an *E. coli* or *P. aeruginosa* biofilm. These methods include contacting the biofilm with an effective amount of the anti-microbial peptide, thereby lysing the *E. coli* or *P. aeruginosa* biofilm.

The disclosed compositions can be administered in conjunction with other agents, such as anti-bacterial or antiviral agents.

The foregoing and other features and advantages of the invention will become more apparent from the following detailed description of a several embodiments which proceeds with reference to the accompanying figures.

SEQUENCE LISTING

Figure 1A:
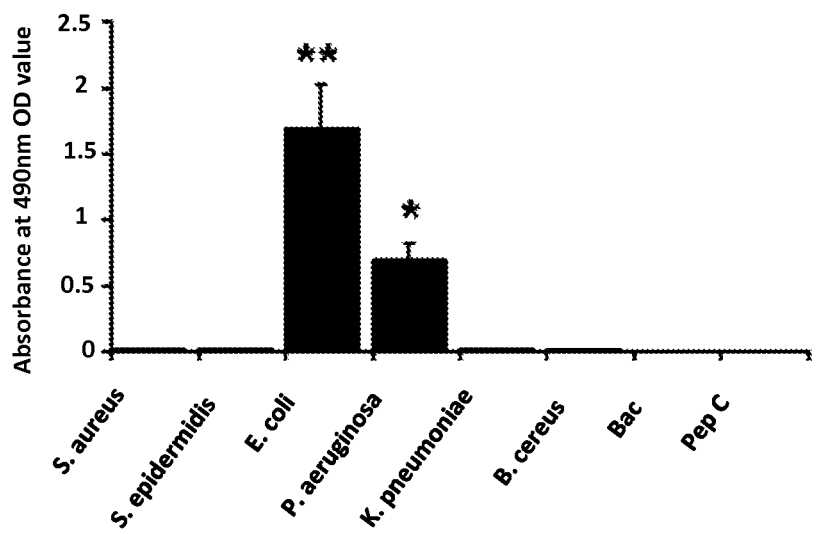
FIGS. 1A-1B. Binding efficiency of EC5 to different bacteria. A. Enzyme Linked Immuno Sorbant assay (ELISA)-based assay—96 well microtiter plates were coated with six bacteria and incubated with the biotinylated peptide and the binding was detected using strepatavidin—horse radish peroxidase (HRP) and developed using 3,3',5,5'-Tetramethylbenzidine (TMB) substrate. (**-p<0.001, *-p<0.05). B. Fluorometry based assay—binding of EC5 to different bacteria was detected using streptavidin-conjugated Q dots. Results are presented as Mean±SD. (**-p<0.0001, *-p<0.001). Bac—Bacteria without peptide, Pep—Peptide without bacteria were used as controls.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file in the form of the file named "Sequence.txt" (4.08 KB), which was created on Feb. 11, 2015, which is incorporated by reference herein. In the accompanying sequence listing:

SEQ ID NOs: 1-3 are synthetic antimicrobial peptides.
SEQ ID NOs: 4-8 are deduced amino acid sequences of phage-displayed peptides.

DETAILED DESCRIPTION OF SEVERAL EMBODIMENTS

Disclosed herein are anti-microbial peptides that can be used to treat or prevent an infection with E. coli and/or P. aeruginosa in a subject, and/or can be used to treat or prevent a viral infection. These anti-microbial peptides can also be used to lyse an E. coli and/or P. aeruginosa biofilm.

Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided:

Animal: Living multi-cellular vertebrate organisms, a category that includes, for example, mammals and birds. The term mammal includes both human and non-human mammals. Similarly, the term "subject" includes both human and veterinary subjects, for example, non-human primates, dogs, cats, horses, rabbits, pigs, mice, rats, and cows.

Anti-bacterial agent: An agent that kills bacteria, or suppresses growth, proliferation, and/or multiplication of bacteria. An anti-bacterial agent includes, but is not limited to, a chemical compound, a small molecule, a peptide mimetic, a peptide, a protein, or a bacteriophage for killing microorganisms or suppressing their multiplication, proliferation, or growth. In some specific embodiments, an anti-bacterial agent is a peptide. In other specific embodiments, an anti-bacterial agent is a chemical compound (an antibiotic).

In one embodiment, anti-bacterial activity can be measured by the production or the size (i.e. diameter of) of a clear zone surrounding a bacterial colony on a bacterial lawn. In another embodiment, an anti-bacterial activity is measured by bacterial cell lysis. In a further embodiment, an anti-bacterial activity is measured by a reduction in bacterial cell viability. A specific, non-limiting example of an agent with anti-bacterial activity includes, but is not limited to, a peptide that has activity against E. coli and/or P. aeruginosa.

Anti-bacterial peptide: A peptide that kills or suppresses growth, proliferation, or multiplication of a bacterial species or particular strain thereof. The peptide can damage the cell wall of the bacteria, disrupt cell membranes associated with the cell wall or within the bacteria, inhibit protein synthesis within the bacteria, or disrupt a sugar backbone.

Antibiotic: A chemical substance, such as one produced by microorganisms, that kills bacteria (bactericidal) and/or inhibits the growth, proliferation, or multiplication of bacteria (bacteriostatic). Exemplary anti-bacterial antibiotics include, but are not limited to, a beta-lactam, a cephalosporin, an aminoglycoside, a sulfonamide, a macrolide, a tetracycline, a silver salt, and the like.

Anti-microbial agent: An agent that kills microorganisms or suppresses their growth, proliferation, or multiplication. An anti-microbial agent includes, but is not limited to, a chemical compound, a small molecule, a peptide mimetic, a peptide, a protein, or a bacteriophage for killing microorganisms or suppressing their proliferation, multiplication or growth of the microbe. In some specific embodiments, an anti-microbial agent is an anti-bacterial agent, an antiviral agent, an antifungal agent, or an antiprotozoal agent. An anti-microbial agent includes both microbiocidal agents (agents that kill a microorganism), as well as those agents (microstatic agents) that inhibit growth or maintain stasis of target microorganisms. In particular embodiments, an anti-microbial agent is an anti-bacterial agent (targets bacteria), see above.

Bacterial infection: Transfer, lodgement and penetration of bacteria, respectively, in a macroorganism such as a human, an animal or a plant and propagation of the bacteria or the protozoa in said macroorganism, see, for example, Pschyrembel (Klinisches Worterbuch, 257. edition, 1994). A bacterial infection which causes pain or suffering in a subject may generally be considered as "bacterial infectious disease". The treatment, amelioration or prevention of a bacterial infection includes the treatment, amelioration or prevention of a disease induced by or related to a bacterial infection or a decrease in the number of bacteria in the subject.

Bioassay: Measurement of the concentration or potency of a substance by its effect on living cells or tissues.

Biofilm: A mass or community of microorganisms attached to a living or non-living surface (such as a surface of a medical device, a tissue, an organ, a household object), and the associated extracellular substances produced by one or more of the attached microorganisms. The extracellular substances are typically polymeric substances that commonly include a matrix of complex polysaccharides, proteinaceous substances and glycopeptides. The microorganisms in a biofilm may include, but are not limited to, bacteria, fungi and protozoa. In a "bacterial biofilm", the microorganisms include one or more species of bacteria. The nature of a biofilm, such as its structure and composition, may depend on the particular species of bacteria present in the biofilm. An established bacterial biofilm is a bacterial biofilm that is recalcitrant to anti-microbial or anti-bacterial treatments that are normally effective at inhibiting or controlling the growth of the corresponding isolated bacteria or planktonic bacteria.

Consists Essentially Of/Consists Of: With regard to a peptide, a peptide that consists essentially of a specified amino acid sequence if it does not include any additional amino acid residues. However, the peptide can include additional non-peptide components, such as labels (for example, fluorescent, radioactive, or solid particle labels), sugars or lipids. With regard to a peptide, a peptide that consists of a specified amino acid sequence does not include any additional amino acid residues, nor does it include additional non-peptide components, such as lipids, sugars or labels.

Contacting: The process of incubating one agent in the presence of another. Thus, when a cell, such as a bacterial cell is contacted with an agent, the cell is incubated with the agent for a sufficient period of time for the agent and the cell to interact.

Effective amount: The "effective amount" of a composition is the quantity of a composition sufficient to achieve a desired result. For instance, this can be the amount of a composition containing a sufficient dose of a peptide sufficient to inhibit the formation of a bacterial biofilm on a surface of an object, or an about to kill or suppress the growth of bacteria. The effective amount of a composition will depend on, for example, the amount of the peptide contained in the composition, the amount of time the composition is in contact with the surface, the temperature at which the interaction between the composition and the surface takes place, and the like.

Gram-negative bacteria: Bacteria that do not retain crystal violet dye in the Gram staining protocol, but take up the counterstain and appear red or pink.

Gram-positive bacteria: Bacteria that are stained dark blue or violet by Gram staining (i.e. the bacteria retain the crystal violet dye).

Host cells: Cells in which a vector can be propagated and its DNA expressed. The cell may be prokaryotic or eukaryotic. The cell can be mammalian, such as a human cell. The term also includes any progeny of the subject host cell. It is understood that all progeny may not be identical to the parental cell since there may be mutations that occur during replication. However, such progeny are included when the term "host cell" is used.

Hydrophobicity Score: A value that defines relative hydrophobicity of the amino acid residues in a peptide. The more positive the value, the more hydrophobic are the amino acids located in the peptide. These scales are commonly used to predict the transmembrane alpha-helices of membrane proteins. The hydrophobicity score can be calculated using the Antimicrobial Peptide Predictor (APD) program (aps.unmc.edu/AP/prediction/prediction_main.php).

Indwelling medical device: A device introduced, inserted, or implanted into a subject for use in the body, such as intravascular catheters (for example, intravenous and intra-arterial), right heart flow-directed catheters, Hickman catheters, arteriovenous fistulae, catheters used in hemodialysis and peritoneal dialysis (for example, silastic, central venous, Tenckhoff, and Teflon catheters), vascular access ports, indwelling urinary catheters, urinary catheters, silicone catheters, ventricular catheters, synthetic vascular prostheses (for example, aortofemoral and femoropopliteal), prosthetic heart valves, prosthetic joints, orthopedic implants, penile implants, shunts (for example, Scribner, Torkildsen, central nervous system, portasystemic, ventricular, ventriculoperitoneal), intrauterine devices, dental implants, stents (for example, ureteral stents), artificial voice prostheses, tympanostomy tubes, gastric feeding tubes, endotracheal tubes, pacemakers, implantable defibrillators, tubing, cannulas, probes, blood monitoring devices, needles, mouth guards, night guards, dentures, orthodontic retainers, contact lenses, and the like. The indwelling medical device can be wholly embedded in the subject (for example, a prosthetic joint, a prosthetic heart valve, or a pacemaker). In some embodiments, the indwelling medical device is partially embedded in the subject and has both internal and external parts, relative to the subject (for example, a urinary catheter, a gastric feeding tube, or a dental implant).

In some embodiments, an indwelling device is surgically implanted (for example, a pacemaker, dental implants, prosthetic joints, vascular prostheses, or shunts). In other embodiments, an indwelling medical device is inserted into the subject by a medical professional using non-surgical means (for example, an intrauterine device, an endotracheal tube, or a urinary catheter). In yet other embodiments, an indwelling medical device includes devices that are routinely inserted and removed by the subject (for example, an inserted medical device) without intervention or aide by a medical professional (for example, a mouth guard, a night guard, removable dentures, an orthodontic retainer, or a contact lens).

Indwelling medical devices can be introduced by any suitable means, for example, by percutaneous, intra-vascular, intra-urethral, intra-orbital, intra-oral, intra-tracheal, intra-esophageal, stomal, or other route, or by surgical implantation, for example intra-articular placement of a prosthetic joint.

Isolated: An "isolated" peptide has been substantially separated or purified away from other peptides and proteins, such as for a naturally occurring peptide from the cell of the organism in which the peptide naturally occurs. With regard to an isolated synthetic peptide, the peptide is substantially free of other peptides. The term "isolated" thus encompasses peptides purified by standard purification methods. The term also embraces peptides prepared by recombinant expression in a host cell as well as chemically synthesized peptides. Similarly, an "isolated" nucleic acid has been substantially separated or purified away from other nucleic acids, such as for a naturally occurring nucleic acid, from the cell of the organism in which protein naturally occurs or has been purified by standard purification methods. The term also embraces nucleic acids prepared by recombinant methods in a host cell as well as chemically synthesized nucleic acids. Examples of isolated nucleic acids or peptides are nucleic acids or peptides that are greater than about 90%, greater than about 95%, greater than about 98%, or greater than about 99% pure.

Inhibiting or treating a disease: Inhibiting a disease, such as a disease caused by a bacterial or viral infection, refers to inhibiting the full development of a disease. In several examples, inhibiting a disease refers to lessening symptoms of the bacterial or viral infection. "Treatment" refers to a therapeutic intervention that ameliorates a sign or symptom of a disease or pathological condition related to the disease, such as a disease caused by a bacteria or a virus.

Label: An agent capable of detection for example by ELISA, spectrophotometry, flow cytometry, or microscopy. For example, a label can be attached to a nucleic acid molecule or protein, thereby permitting detection of the nucleic acid molecule or protein. Examples of labels include, but are not limited to, radioactive isotopes, co-factors, ligands, fluorophores, haptens, enzymes, and combinations thereof. Methods for labeling and guidance in the choice of labels appropriate for various purposes are discussed for example in Sambrook et al.

(Molecular Cloning: A Laboratory Manual, Cold Spring Harbor, N.Y., 1989) and Ausubel et al. (In Current Protocols in Molecular Biology, John Wiley & Sons, New York, 1998).

In some embodiments, the label is a fluorophore ("fluorescent label"). Fluorophores are chemical compounds, which when excited by exposure to a particular wavelength of light, emit light (i.e., fluoresce) at a different wavelength. Fluorophores can be described in terms of their emission profile, or "color". Green fluorophores, for example Cy3, FITC, and Oregon Green, are characterized by their emission at wavelengths generally in the range of 515-540 nanometers (nm). Red fluorophores, for example Texas Red, Cy5 and tetramethylrhodamine, are characterized by their emission at wavelengths generally in the range of 590-690 nm. In other embodiments, the label is a protein tag recognized by an antibody, for example a histidine (His)-tag, a hemagglutinin (HA)-tag, or a c-Myc-tag.

Lumen: The cavity or channel within a tube, pipe, or other tubular device.

Medical device: Medical devices are objects associated with the administration of a therapy to a user. Examples of a medical device include medical infusion pumps, pulse oximeters, cardiopulmonary monitors, hemodialysis systems, and other therapy delivery and patient monitoring equipment. In some embodiments, a medical device refers to an object that is designed to be placed partially or wholly within a subject's body (an indwelling medical device, such as a device that is suitable for surgical implantation within the body) for one or more therapeutic or prophylactic purposes, such as for restoring physiological function, alleviating symptoms associated with disease, delivering therapeutic agents, detecting changes (or levels) in the internal environment, and/or repairing or replacing or augmenting damaged or diseased organs and tissues. Not all medical devices need have direct therapeutic activity. The device can be, for example, a storage device, such as a medical storage device, such as a container for a contact lens.

Peptide Modifications: Anti-microbial peptides include synthetic embodiments of peptides described herein. In addition, analogues (non-peptide organic molecules), derivatives (chemically functionalized peptide molecules obtained starting with the disclosed peptide sequences) and variants (homologs) of these proteins can be utilized in the methods described herein.

Peptides may be modified by a variety of chemical techniques to produce derivatives having essentially the same activity as the unmodified peptides, and optionally having other desirable properties. For example, carboxylic acid groups of the protein, whether carboxyl-terminal or side chain, may be provided in the form of a salt of a pharmaceutically-acceptable cation or esterified to form a $C_1$-$C_{16}$ ester, or converted to an amide of formula $NR_1R_2$ wherein $R_1$ and $R_2$ are each independently H or $C_1$-$C_{16}$ alkyl, or combined to form a heterocyclic ring, such as a 5- or 6-membered ring. Amino groups of the peptide, whether amino-terminal or side chain, may be in the form of a pharmaceutically-acceptable acid addition salt, such as the HCl, HBr, acetic, benzoic, toluene sulfonic, maleic, tartaric and other organic salts, or may be modified to $C_1$-$C_{16}$ alkyl or dialkyl amino or further converted to an amide.

Hydroxyl groups of the peptide side chains may be converted to $C_1$-$C_{16}$ alkoxy or to a $C_1$-$C_{16}$ ester using well-recognized techniques. Phenyl and phenolic rings of the peptide side chains may be substituted with one or more halogen atoms, such as fluorine, chlorine, bromine or iodine, or with $C_1$-$C_{16}$ alkyl, $C_1$-$C_{16}$ alkoxy, carboxylic acids and esters thereof, or amides of such carboxylic acids. Methylene groups of the peptide side chains can be extended to homologous $C_2$-$C_4$ alkylenes. Thiols can be protected with any one of a number of well-recognized protecting groups, such as acetamide groups. Those skilled in the art will also recognize methods for introducing cyclic structures into the peptides of this invention to select and provide conformational constraints to the structure that result in enhanced stability.

Peptidomimetic and organomimetic embodiments are envisioned, whereby the three-dimensional arrangement of the chemical constituents of such peptido- and organomimetics mimic the three-dimensional arrangement of the peptide backbone and component amino acid side chains, resulting in such peptido- and organomimetics of an anti-microbial peptide having measurable or enhanced anti-microbial activity. For computer modeling applications, a pharmacophore is an idealized, three-dimensional definition of the structural requirements for biological activity. Peptido- and organomimetics can be designed to fit each pharmacophore with current computer modeling software (using computer assisted drug design or CADD). See Walters, "Computer-Assisted Modeling of Drugs", in Klegerman & Groves, eds., 1993, *Pharmaceutical Biotechnology*, Interpharm Press: Buffalo Grove, Ill., pp. 165-174 and *Principles of Pharmacology*

Munson (ed.) 1995, Ch. 102, for descriptions of techniques used in CADD. Also included are mimetics prepared using such techniques.

Pharmaceutically acceptable carriers: Conventional pharmaceutically acceptable carriers are useful for practicing the methods and forming the compositions disclosed herein. *Remington's Pharmaceutical Sciences*, by E. W. Martin, Mack Publishing Co., Easton, Pa., 15th Edition, 1975, describes examples of compositions and formulations suitable for pharmaceutical delivery of the peptides herein disclosed.

In general, the nature of the carrier will depend on the particular mode of administration being employed. For example, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Peptide and Polyeptide: A polymer in which the monomers are amino acid residues that are joined together through amide bonds. When the amino acids are alpha-amino acids, either the L-optical isomer or the D-optical isomer can be used, the L-isomers being preferred in nature. The terms peptide and polypeptide are specifically intended to cover naturally occurring molecules, as well as those that are recombinantly or synthetically produced. In some embodiments, a peptide or polypeptide is at least 5 and at most 15, 25, 50, 75, or 100 amino acids in length.

Substantially purified peptide or substantially purified peptide or polypeptide as used herein refers to a peptide or polypeptide that is substantially free of other proteins, lipids, carbohydrates or other materials with which it is naturally associated. In one embodiment, the peptide or polypeptide is at least 80% free of other proteins, lipids, carbohydrates or other materials with which it is naturally associated. In another embodiment, the peptide or polypeptide is at least 90% free of other proteins, lipids, carbohydrates or other materials with which it is naturally associated. In yet another embodiment, the peptide or polypeptide is at least 95% free of other proteins, lipids, carbohydrates or other materials with which it is naturally associated.

Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

A non-conservative amino acid substitution can result from changes in: (a) the structure of the amino acid backbone in the area of the substitution; (b) the charge or hydrophobicity of the amino acid; or (c) the bulk of an amino acid side chain. Substitutions generally expected to produce the greatest changes in protein properties are those in which: (a) a hydrophilic residue is substituted for (or by) a hydrophobic residue; (b) a proline is substituted for (or by) any other residue; (c) a residue having a bulky side chain, e.g., phenylalanine, is substituted for (or by) one not having a side chain, e.g., glycine; or (d) a residue having an electropositive side chain, e.g., lysyl, arginyl, or histadyl, is substituted for (or by) an electronegative residue, e.g., glutamyl or aspartyl.

Variant amino acid sequences may, for example, be 80, 90 or even 95 or 98% identical to the native amino acid sequence. Programs and algorithms for determining percentage identity can be found at the NCBI website.

Purified: The term "purified" does not require absolute purity; rather, it is intended as a relative term. Thus, for example, a purified protein preparation is one in which the protein referred to is more pure than the protein in its natural environment within a cell. For example, a preparation of a protein can be purified such that the protein represents at least 50%, 80%, 90%, 95% or 99% of the total protein content of the preparation. Similarly, a purified oligonucleotide preparation is one in which the oligonucleotide is more pure than in an environment including a complex mixture of oligonucleotides.

Sequence identity: The similarity between two nucleic acid sequences or between two amino acid sequences is expressed in terms of the level of sequence identity shared between the sequences. Sequence identity is typically expressed in terms of percentage identity; the higher the percentage, the more similar the two sequences.

Methods for aligning sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. USA* 85:2444, 1988; Higgins and Sharp, *Gene* 73:237-244, 1988; Higgins and Sharp, *CABIOS* 5:151-153, 1989; Corpet et al., *Nucleic Acids Research* 16:10881-10890, 1988; Huang, et al., *Computer Applications in the Biosciences* 8:155-165, 1992; Pearson et al., *Methods in Molecular Biology* 24:307-331, 1994; Tatiana et al., (1999), *FEMS Microbiol. Lett.,* 174:247-250, 1999. Altschul et al. present a detailed consideration of sequence-alignment methods and homology calculations (*J. Mol. Biol.* 215:403-410, 1990).

The National Center for Biotechnology Information (NCBI) Basic Local Alignment Search Tool (BLAST™, Altschul et al. *J. Mol. Biol.* 215:403-410, 1990) is available from several sources, including the National Center for Biotechnology Information (NCBI, Bethesda, Md.) and on the Internet, for use in connection with the sequence-analysis programs blastp, blastn, blastx, tblastn and tblastx. A description of how to determine sequence identity using this program is available on the internet under the help section for BLAST™.

Sterile: Free from living organisms and especially microorganisms such as bacteria, fungi, viruses, and protozoa.

Subject: An animal or human subjected to a treatment, observation or experiment.

Treating or Treatment: A prescribed course of action (including administration of an agent, such as an anti-microbial agent, antiviral agent, or an anti-bacterial agent) to alter the normal course of an existing infection caused by a microorganism (for example, surface attached bacteria, such as a biofilm). In some embodiments, the prescribed course of action is to inhibit further growth (or proliferation or multiplication) of, or control the growth (or proliferation or multiplication) of surface attached bacteria (for example, bacteria in a biofilm). In one embodiment, treating or treatment includes a prescribed course of action on the microorganism susceptible to the treatment (for example, surface attached bacteria). In another embodiment, treating or treatment includes a prescribed course of action to a subject that has a biofilm, either on a living surface and/or on an implanted medical device. In other embodiments, treating or treatment includes a prescribed course of action to a living surface (for example, a bone, a joint, an organ, an organ cavity, or a tissue in a subject) or a non-living surface (for example, a surface of a medical device), that contains or is in contact with the microorganism susceptible to the treatment.

Therapeutically effective dose: A dose sufficient to prevent advancement, or to cause regression of the disease, or which is capable of relieving symptoms caused by the disease. The dose can also be sufficient to cause lysis of bacteria, suppress or reduce bacterial growth, reduce viral titer, and reduce or prevent biofilm formation. In one embodiment, a therapeutically effective dose is a dose sufficient to prevent advancement or relieve symptoms of a bacterial or viral infection.

Vector: A nucleic acid molecule as introduced into a host cell, thereby producing a transduced or transformed host cell. A vector may include nucleic acid sequences that permit it to replicate in a host cell, such as an origin of replication. A vector may also include one or more selectable marker gene and other genetic elements known in the art. Vectors include plasmid vectors, including plasmids for expression in Gram-negative and Gram-positive bacterial cells. Common vectors include those for expression in $E.$ $coli$ and $Salmonella$. Vectors also include viral vectors, such as, but not limited to, retrovirus, orthopox, avipox, fowlpox, capripox, suipox, adenoviral, herpes virus, alpha virus, baculovirus, Sindbis virus, vaccinia virus and poliovirus vectors. Vectors also include vectors for expression in yeast cells Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the use of A or B is intended to include the use of A, the use of B, or the use of A and B. It is further to be understood that all base sizes or amino acid sizes, and all molecular weight or molecular mass values, given for nucleic acids or peptides are approximate, and are provided for description. Although methods and materials similar or equivalent to those described herein can be used in the practice or testing of this disclosure, suitable methods and materials are described below. The term "comprises" means "includes". All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Peptides with Anti-Microbial Activity

Disclosed herein are isolated synthetic peptides that have anti-microbial activity against $E.$ $coli$ and $P.$ $aeruginosa$. These peptides can be used to treat a subject with an $E.$ $coli$ or $P.$ $aeruginosa$ infection, or can be used to lyse an $E.$ $coli$ and $P.$ $aeruginosa$ biofilm, such as, but not limited to a biofilm on a medical device. These peptides are also of use for treating viral infections. The peptides are 9 to 15 amino acids in length, and have a hydrophobicity score from about 40% to about 60%, a net charge of +5 to +7. This can be calculated, for example, using the APD program (see above). The anti-microbial peptides disclosed herein can be used alone or in combination with other anti-microbial peptides or other therapeutic agents, such as anti-bacterial or anti-viral agents.

In some embodiments, the peptides have a hydrophobicity score from about 40% to about 50%, such as from about 40% to about 45%, or from about 40% to about 43%. Thus, the peptide can have a hydrophobicity score of 40%, 41%, 42%, 43%, 44%, 45%, 46%, 47%, 48%, 49% or 50%. In other embodiments, the peptides have a net charge of about +5 to about +7, such as +5, +6, or +7. As noted above, the peptide can be 9 to 15 amino acids in length, such as 9 to 12 amino acids in length, 12 to 15 amino acids in length, or 10 to 14 amino acids in length. The peptide can be 9, 10, 11, 12, 13, 14 or 15 amino acids in length.

In some embodiments, the isolated peptide is 9 to 15 amino acids in length, and includes the amino acid sequence set forth as:

$X_1X_2LFX_3X_4X_5X_6X_7X_8X_9X_{10}$ (SEQ ID NO: 1)

wherein $X_1$ is R or W, $X_2$ is L, C or no amino acid; $X_3$ is R or no amino acid; $X_4$ is K, C or no amino acid; $X_5$ is I or no amino acid; $X_6$ is R or no amino acid; $X_7$ is R, C or no amino acid; $X_8$ is L or no amino acid; $X_9$ is K or no amino acid; and $X_{10}$ is R or W. As disclosed above, the peptide has a hydrophobicity score of 40%-60%, a net charge of +5 to +7, and has anti-microbial activity against $E.$ $coli$ and/or $P.$ $aeruginosa$.

In additional embodiments, the peptide includes the amino acid sequence set forth as:

$X_{11}X_{12}X_{13}X_1X_2LFX_3X_4X_5X_6X_7X_8X_9X_{10}X_{14}X_{15}W$ (SEQ ID NO: 2)

wherein the N-terminal amino acid is an R; wherein $X_{11}$ is R or no amino acid; $X_{12}$ is R,C,A, W or no amino acid; $X_{13}$ is R,C,A, W or no amino acid; $X_{14}$, is C,A, W or no amino acid; and $X_{15}$ C,A,W or no amino acid. As disclosed above, the peptide has a hydrophobicity score of 40%-60%, a net charge of +5 to +7, and has anti-microbial activity against $E.$ $coli$ and/or $P.$ $aeruginosa$.

In some examples, the amino acid sequence set forth as:

$X_1LLFRKIRRLKX_{10}$ (SEQ ID NO: 1, wherein $X_1$ is R or W; $X_2$ is L; $X_3$ is R or no amino acid; $X_4$ is K; $X_5$ is I; $X_6$ is R; $X_7$ is R; $X_8$ is L; and $X_9$ is K; and wherein and $X_{10}$ is R or W). In some examples, $X_1$ is R and $X_{10}$ is R or W. In other examples, $X_1$ is R or W and $X_{10}$ is R or W.

Exemplary peptides include, or consist of:

a) RLLFRKIRRLKR (SEQ ID NO: 1, wherein $X_1$ is R; $X_2$ is L; $X_3$ is R; $X_4$ is K; $X_5$ is I; $X_6$ is R; $X_7$ is R; $X_8$ is L; and $X_9$ is K and $X_{10}$ is R);

b) WLLFRKIRRLKW (SEQ ID NO: 1, wherein $X_1$ is W; $X_2$ is L; $X_3$ is R; $X_4$ is K; $X_5$ is I; $X_6$ is R; $X_7$ is R; $X_8$ is L; and $X_9$ is K and $X_{10}$ is W);

c) RLARLLFRKIRRLKR (SEQ ID NO: 2, wherein $X_1$ is R; $X_2$ is L; $X_3$ is R; $X_4$ is K; $X_5$ is I; $X_6$ is R; $X_7$ is R; $X_8$ is L; and $X_9$ is K and $X_{10}$ is R, $X_{11}$ is R, $X_{12}$ is L; $X_{13}$ is A; and $X_{14}$, $X_{15}$ and $X_{16}$ are no amino acid);

d) RLLFRKIRRLKRCAW (SEQ ID NO: 2, wherein $X_1$ is R; $X_2$ is L; $X_3$ is R; $X_4$ is K; $X_5$ is I; $X_6$ is R; $X_7$ is R; $X_8$ is L; and $X_9$ is K and $X_{10}$ is R, $X_{11}$, $X_{12}$ and $X_{13}$ are no amino acid; $X_{14}$ is C $X_{15}$ is A and $X_{16}$ is W); or e) RCLFRKIRRLKR (SEQ ID NO: 1, wherein $X_1$ is R; $X_2$ is C; $X_3$ is R; $X_4$ is K; $X_5$ is I; $X_6$ is R; $X_7$ is R; $X_8$ is L; and $X_9$ is K and $X_{10}$ is R).

In one specific non-limiting example, the peptide consists of consisting of the amino acid sequence set forth as RLL-FRKIRRLKR (SEQ ID NO: 1, wherein $X_1$ is R; $X_2$ is L; $X_3$ is R; $X_4$ is K; $X_5$ is I; $X_6$ is R; $X_7$ is R; $X_8$ is L; and $X_9$ is K and $X_{10}$ is R, also set forth as SEQ ID NO: 3

Additional exemplary peptides include, or consist of:

f) RLFRKIRLR (SEQ ID NO: 1 wherein $X_1$ is R, $X_2$ is no amino acid; $X_3$ is R; $X_4$ is K; $X_5$ is I; $X_6$ is no amino acid; $X_7$ is R; $X_8$ is L; $X_9$ is no amino acid; and $X_{10}$ is R);

g) RLLFKIRKR (SEQ ID NO: 1, wherein $X_1$ is R, $X_2$ is L; $X_3$ is no amino acid; $X_4$ is K; $X_5$ is I; $X_6$ is R; $X_7$ is no amino acid; $X_8$ is no amino acid; $X_9$ is K; and $X_{10}$ is R);

h) RLLFRRLKR (SEQ ID NO: 1, wherein $X_1$ is R, $X_2$ is L; $X_3$ is no amino acid; $X_4$ is no amino acid; $X_5$ is no amino acid; $X_6$ is R; $X_7$ is R; $X_8$ is L; $X_9$ is K; and $X_{10}$ is W); or i) RLLFRRLKR (SEQ ID NO: 1, wherein $X_1$ is R, $X_2$ is L; $X_3$ is R; $X_4$ is no amino acid; $X_5$ is no amino acid; $X_6$ is no amino acid; $X_7$ is R; $X_8$ is L; $X_9$ is K; and $X_{10}$ is R or W.

The anti-microbial peptides disclosed herein can be chemically synthesized by standard methods, or can be produced recombinantly. An exemplary process for peptide production is described in Lu et al., *Federation of European Biochemical Societies Letters*. 429:31-35, 1998. They can also be isolated by methods including preparative chromatography and immunological separations. If desired, anti-microbial peptides can also be chemically synthesized by other technologies. One such process is described in W. Lu et al., *Federation of European Biochemical Societies Letters*. 429:31-35, 1998. Peptides can also be produced using molecular genetic techniques, such as by inserting a nucleic acid encoding the anti-microbial peptide into an expression vector, introducing the expression vector into a host cell, and isolating the peptide (see below).

These polynucleotides encoding the anti-microbial peptide include DNA, cDNA and RNA sequences which encode the peptide of interest. Silent mutations in the coding sequence result from the degeneracy (i.e., redundancy) of the genetic code, whereby more than one codon can encode the same amino acid residue. Thus, for example, leucine can be encoded by CTT, CTC, CTA, CTG, TTA, or TTG; serine can be encoded by TCT, TCC, TCA, TCG, AGT, or AGC; asparagine can be encoded by AAT or AAC; aspartic acid can be encoded by GAT or GAC; cysteine can be encoded by TGT or TGC; alanine can be encoded by GCT, GCC, GCA, or GCG; glutamine can be encoded by CAA or CAG; tyrosine can be encoded by TAT or TAC; and isoleucine can be encoded by ATT, ATC, or ATA. Tables showing the standard genetic code can be found in various sources (e.g., L. Stryer, 1988, Biochemistry, $3^{rd}$ Edition, W.H. 5 Freeman and Co., NY).

A nucleic acid encoding an anti-microbial peptide can be cloned or amplified by in vitro methods, such as the polymerase chain reaction (PCR), the ligase chain reaction (LCR), the transcription-based amplification system (TAS), the self-sustained sequence replication system (3SR) and the Qβ replicase amplification system (QB). For example, a polynucleotide encoding the protein can be isolated by polymerase chain reaction of cDNA using primers based on the DNA sequence of the molecule. A wide variety of cloning and in vitro amplification methodologies are well known to persons skilled in the art. PCR methods are described in, for example, U.S. Pat. No. 4,683,195; Mullis et al., *Cold Spring Harbor Symp. Quant. Biol.* 51:263, 1987; and Erlich, ed., *PCR Technology*, (Stockton Press, NY, 1989). Polynucleotides also can be isolated by screening genomic or cDNA libraries with probes selected from the sequences of the desired polynucleotide under stringent hybridization conditions.

The polynucleotides encoding an anti-microbial peptide include a recombinant DNA which is incorporated into a vector, into an autonomously replicating plasmid or virus, or into the genomic DNA of a prokaryote or eukaryote, or which exists as a separate molecule (such as a cDNA) independent of other sequences. The nucleotides of the invention can be ribonucleotides, deoxyribonucleotides, or modified forms of either nucleotide. The term includes single and double forms of DNA.

In one embodiment, vectors are used for expression in yeast such as *S. cerevisiae*, *Pichia pastoris* or *Kluyveromyces lactis*. Several promoters are known to be of use in yeast expression systems such as the constitutive promoters plasma membrane $H^+$-ATPase (PMA1), glyceraldehyde-3-phosphate dehydrogenase (GPD), phosphoglycerate kinase-1 (PGK1), alcohol dehydrogenase-1 (ADH1), and pleiotropic drug-resistant pump (PDR5). In addition, many inducible promoters are of use, such as GAL1-10 (induced by galactose), PHO5 (induced by low extracellular inorganic phosphate), and tandem heat shock HSE elements (induced by temperature elevation to 37° C.). Promoters that direct variable expression in response to a titratable inducer include the methionine-responsive METS and MET25 promoters and copper-dependent CUP1 promoters. Any of these promoters may be cloned into multicopy (20 or single copy (CEN) plasmids to give an additional level of control in expression level. The plasmids can include nutritional markers (such as URA3, ADE3, HIS1, and others) for selection in yeast and antibiotic resistance (AMP) for propagation in bacteria. Plasmids for expression on *K lactis* are known, such as pKLAC1. Thus, in one example, after amplification in bacteria, plasmids can be introduced into the corresponding yeast auxotrophs by methods similar to bacterial transformation.

The anti-microbial peptides can be expressed in a variety of yeast strains. For example, seven pleiotropic drug-resistant transporters, YOR1, SNQ2, PDR5, YCF1, PDR10, PDR11, and PDR15, together with their activating transcription factors, PDR1 and PDR3, have been simultaneously deleted in yeast host cells, rendering the resultant strain sensitive to drugs. Yeast strains with altered lipid composition of the plasma membrane, such as the erg6 mutant defective in ergosterol biosynthesis, can also be utilized. Proteins that are highly sensitive to proteolysis can be expressed in yeast strains lacking the master vacuolar endopeptidase Pep4, which controls the activation of other vacuolar hydrolases. Heterologous expression in strains carrying temperature-sensitive (ts) alleles of genes can be employed if the corresponding null mutant is inviable.

Viral vectors can also be prepared encoding the anti-microbial peptides disclosed herein. A number of viral vectors have been constructed, including polyoma, SV40 (Madzak et al., 1992, J. Gen. Virol., 73:15331536), adenovirus (Berkner, 1992, Cur. Top. Microbiol. Immunol., 158:39-6; Berliner et al., 1988, Bio Techniques, 6:616-629; Gorziglia et al., 1992, J. Virol., 66:4407-4412; Quantin et al., 1992, Proc. Nad. Acad. Sci. USA, 89:2581-2584; Rosenfeld et al., 1992, Cell, 68:143-155; Wilkinson et al., 1992, Nucl. Acids Res., 20:2233-2239; Stratford-Perricaudet et al., 1990, Hum. Gene Ther., 1:241-256), vaccinia virus (Mackett et al., 1992, Biotechnology, 24:495-499), adeno-associated virus (Muzyczka, 1992, Curr. Top. Microbiol. Immunol., 158:91-123; On et al., 1990, Gene, 89:279-282), herpes viruses including HSV and EBV (Margolskee, 1992, Curr. Top. Microbiol. Immunol., 158:67-90; Johnson et al., 1992, J. Virol., 66:29522965; Fink et al., 1992, Hum. Gene Ther. 3:11-19; Breakfield et al., 1987, Mol. Neurobiol., 1:337-371; Fresse et al., 1990, Biochem. Pharmacol., 40:2189-2199), Sindbis viruses (H. Herweijer et al., 1995, Human Gene Therapy 6:1161-1167; U.S. Pat. No. 5,091,309 and U.S. Pat. No. 5,2217,879), alphaviruses (S. Schlesinger, 1993, Trends Biotechnol. 11:18-22; I. Frolov et al., 1996, Proc. Natl. Acad. Sci. USA 93:11371-11377) and retroviruses of avian (Brandyopadhyay et al., 1984, Mol. Cell Biol., 4:749-754; Petropouplos et al., 1992, J. Virol., 66:3391-3397), murine (Miller, 1992, Curr. Top. Microbiol. Immunol., 158:1-24; Miller et al., 1985, Mol. Cell Biol., 5:431-437; Sorge et al., 1984, Mol. Cell Biol., 4:1730-1737; Mann et al., 1985, J. Virol., 54:401-407), and human origin (Page et al., 1990, J. Virol., 64:5370-5276; Buchschalcher et al., 1992, J. Virol., 66:2731-2739). Baculovirus (*Autographa californica* multinuclear polyhedrosis virus; AcMNPV) vectors are also known in the art, and may be obtained from commercial sources (such as PharMingen, San Diego, Calif.; Protein Sciences Corp., Meriden, Conn.; Stratagene, La Jolla, Calif.).

Thus, in one embodiment, the polynucleotide encoding an anti-microbial peptide is included in a viral vector. Suitable vectors include retrovirus vectors, orthopox vectors, avipox vectors, fowlpox vectors, capripox vectors, suipox vectors, adenoviral vectors, herpes virus vectors, alpha virus vectors, baculovirus vectors, Sindbis virus vectors, vaccinia virus vectors and poliovirus vectors. Specific exemplary vectors are poxvirus vectors such as vaccinia virus, fowlpox virus and a highly attenuated vaccinia virus (MVA), adenovirus, baculovirus and the like. In some embodiments, isolated host cells, such as eukaryotic host cells, can be transformed with these vectors, and the anti-microbial peptides can be isolated from the host cells. The anti-microbial peptides can then be formulated into compositions for use either in vivo or in vitro.

Pharmaceutical Compositions and Methods of Treatment

The anti-microbial peptides disclosed herein can be included in a pharmaceutical composition for administration to a subject. In particular, disclosed herein are compositions, such as pharmaceutical compositions, for use in treating and/or inhibiting an infection by *E. coli, P. aeruginosa*, and/or a virus, for use in the manufacture of a medicament, and/or for use as medicament. The anti-microbial composition can also be formulated for the treatment of a biofilm, such as on the surface of a medical device (see below), such as an indwelling medical device. The anti-microbial peptides can be used individually or in combination. Thus, 2, 3, 4, 5, or more of the anti-microbial peptides disclosed herein can be used in combination. The anti-microbial peptides can also be used in combination with other anti-viral and/or anti-bacterial agents.

In some examples, a subject is selected for treatment that has or is at risk for developing an infection by *E. coli* and/or *P. aeruginosa*. In one embodiment, the agents described herein may be used for the treatment, amelioration or prevention of a disease induced by or related to a bacterial infection. The compound may also be used for the treatment, amelioration and prevention of a bacterial infection even if the infection does not cause pain or suffering in a subject. The agents disclosed herein may also be used against bacterial strains with resistance to antibiotics. The method include selecting a subject with a *E. coli* and/or *P. aeruginosa* infection, and administering to the subject a therapeutically effective amount of one or more of the anti-microbial peptides disclosed herein, thereby treating the *E. coli* and/or *P. aeruginosa* infection in the subject.

The anti-microbial peptides disclosed herein are also of use to treat viral infections. The methods include selecting a subject with a viral infection, and administering to the subject a therapeutically effective amount of one or more of the anti-microbial peptides disclosed herein. The virus can be a member of the following viral families:

1. DNA viruses: Adenoviridae, Papillomaviridae, Herpesviridae, Poxviridae, Polyomaviridae, and Anneloviridae.
2. RNA viruses: Reoviridae, Picornaviridae, Caliciviridae, Togaviridiae, Arenaviridae, Flaviviridae, Orthomyxoviridae, Paramyxoviridae, Bunyaviridae, Rhabdoviridae, Filoviridae, Coronaviridae, Astroviridae, Bornaviridae, Arteriviridae, and Hepeviridae
3. Reverse Transcribing virus: Lentiviridae (including human immunodeficiency virus) and Hepatitis Viruses In some embodiments, the virus can infect humans. The virus can be a double-stranded DNA virus, such as a Herpesviridae (for example, a Herpes Simplex Virus (HSV), Varicellovirus, Cytomegalovirus (CMV), Roseolovirus, Lymphocrtytovirus, or Rhadinovirus), an Adenoviridae (for example, a Mastadenovirus), a Papillomadviridae (for example, an Alphapapillomavirus, Betapapillomavirus, Gammapapillomavirus, Mupapillomavirus, or Nupapillomavirus). In other embodiments, the virus is a single-stranded DNA virus, such as Anelloviridae (for example, Alphatorquevirus, Betatorquevirus, Gammatorquevirus) or Parvovirdae (for example, Erythrovirus, Dependovirus or Bacavirus). The virus can be a double-stranded RNA virus, such as Reovirdiae (for example, Coltivirus, Rotavirus, or Seadomavirus). The virus can be a positive, single-stranded RNA virus, such as a Hepevirus, a Coronaviridae (for example, Alphacoronavirus, Betacoronavirus, Torovirus, HEV), Astroviridae (for example, Mamastrovirus), Calciviridae (for example, Norovirus, Sapovirus), Flaviviridae (for example, Flavavirus, Hepacivirus), Picornaviridae (for example, Cardiovirus, Enterovirus, Hepatovirus, Kobuvirus, and Parechovirus), or Togaviridae (for example, Alphavirus and Rubivirus). The virus can be a negative, single-stranded RNA virus, such as Deltavirus, Rhabdoviridae (for example, Lyssa virus, Vesiculovirus), Filoviridae (for example, Ebola virus and Marburg virus), Paramyxoviridae (for example, Henipavirus, Morbilivirus, Respirovirus, Rubulavirus, Metapneumovirus, and Pneumovirus), Arenaviridae (Arenavirus), Bunyaviridae (for example, Hantavirus, Nairovirus, Orthobunyavirus and Plebovirus), or Orthomyxoviridae (for example, Influenza A, Influenza B, Influenza C and Thogotovirus). The virus can be a retro-transcribing virus, such as Retroviridae (for example, Gammaretrovirus, Deltaretrovirus, Lentivirus and Spumavirus) or Hepadnaviridae (for example, Orthohepadnavirus).

In some embodiments, the virus is a lentivirus, retrovirus, adenovirus, poxvirus, influenza virus, herpesvirus, papillomavirus, hepatitis virus, or polyoma virus. In some embodiment, methods are provided for treating an infection with a vaccinia, influenza A, rotavirus, or rubella virus.

In accordance with the various treatment methods of the disclosure, the anti-microbial peptide can be delivered to a subject in a manner consistent with conventional methodologies associated with management of the disorder for which treatment or prevention is sought. In accordance with the disclosure herein, a prophylactically or therapeutically effective amount of the anti-microbial peptide is administered to a subject in need of such treatment for a time and under conditions sufficient to prevent, inhibit, and/or ameliorate a selected disease or condition or one or more symptom(s) thereof.

The administration of the anti-microbial peptide can be for either prophylactic or therapeutic purpose. When provided prophylactically, the anti-microbial peptide is provided in advance of any symptom. The prophylactic administration of the anti-microbial peptide serves to prevent or ameliorate any subsequent disease process. When provided therapeutically, the compound is provided at (or shortly after) the onset of a symptom of disease or infection.

For use in treatment, one or more of the anti-microbial peptides disclosed herein can be administered systemically or locally. The anti-microbial peptide(s) can be administered to subjects by a variety of administration modes, including by oral, rectal, intranasal, intrapulmonary, or transdermal delivery, or by topical delivery. Optionally, the anti-microbial peptide(s) can be administered by non-mucosal routes, including by intramuscular, subcutaneous, intravenous, intra-arterial, intra-articular, intraperitoneal, intrathecal, intracerebroventricular, or parenteral routes.

For prophylactic and therapeutic purposes, the anti-microbial peptide can be administered to the subject by the oral route or in a single bolus delivery, via continuous delivery (for example, continuous transdermal, mucosal or intravenous delivery) over an extended time period, or topically. In some embodiments, one or more of the anti-microbial peptides are used in a repeated administration protocol (for example, by an hourly, daily or weekly, repeated administration protocol). The anti-microbial peptides disclosed herein can be administered in combination, such that two, three, four or more anti-microbial peptides are administered together. Thus, any of the methods disclosed herein can utilize more than one anti-microbial peptide.

The therapeutically effective dosage of the anti-microbial peptide can be provided as repeated doses within a prolonged prophylaxis or treatment regimen that will yield clinically significant results to alleviate one or more symptoms or detectable conditions associated with a targeted disease or condition as set forth herein. Determination of effective dosages in this context is typically based on animal model studies followed up by human clinical trials and is guided by administration protocols that significantly reduce the occurrence or severity of targeted disease symptoms or conditions in the subject. Suitable models in this regard include, for example, murine, rat, avian, porcine, feline, non-human primate, and other accepted animal model subjects known in the art. Alternatively, effective dosages can be determined using in vitro models. Using such models, only ordinary calculations and adjustments are required to determine an appropriate concentration and dose to administer a therapeutically effective amount of the anti-microbial peptide (for example, amounts that are effective to elicit a desired immune response or alleviate one or more symptoms of a targeted infection).

The actual dosage of the agents will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the anti-microbial peptide and formulation. Dosage regimens can be adjusted to provide an optimum prophylactic or therapeutic response. A therapeutically effective amount is also one in which any toxic or detrimental side effects of the agent are outweighed in clinical terms by therapeutically beneficial effects.

A non-limiting range for a therapeutically effective amount of an agent within the methods and formulations of the disclosure is about 0.01 mg/kg body weight to about 20 mg/kg body weight, such as about 0.05 mg/kg to about 5 mg/kg body weight, or about 0.2 mg/kg to about 2 mg/kg body weight. Dosage can be varied by the attending clinician to maintain a desired concentration at a target site (for example, the lungs or systemic circulation). Higher or lower concentrations can be selected based on the mode of delivery, for example, topical, trans-epidermal, rectal, oral, pulmonary, or intranasal delivery versus intravenous or subcutaneous delivery. Dosage can also be adjusted based on the release rate of the administered formulation, for example, of an intrapulmonary spray versus powder, sustained release oral versus injected particulate or transdermal delivery formulations, and so forth.

The pharmaceutical compositions for administration to a subject can include at least one further pharmaceutically acceptable additive such as carriers, thickeners, diluents, buffers, preservatives, surface active agents and the like in addition to the molecule of choice. Pharmaceutical compositions can also include one or more additional active ingredients such as anti-microbial agents, anti-inflammatory agents, anesthetics, and the like. The pharmaceutically acceptable carriers useful for these formulations are conventional. *Remington's Pharmaceutical Sciences*, by E. W. Martin, Mack Publishing Co., Easton, Pa., 19th Edition (1995), describes compositions and formulations suitable for pharmaceutical delivery of the compounds herein disclosed.

In general, the nature of the carrier will depend on the particular mode of administration being employed. For instance, parenteral formulations usually contain injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate. The compositions can contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate. For solid compositions, conventional non-toxic pharmaceutically acceptable vehicles can be used which include, for example, pharmaceutical grades of mannitol, lactose, starch, magnesium stearate, sodium saccharin, talcum, cellulose, glucose, sucrose, magnesium carbonate, and the like.

To formulate the pharmaceutical compositions or for the treatment of a biofilm, the anti-microbial peptides (see below) can be combined with various pharmaceutically acceptable additives, as well as a base or vehicle for dispersion of the compound. Desired additives include, but are not limited to, pH control agents, such as arginine, sodium hydroxide, glycine, hydrochloric acid, citric acid, and the like. In addition, local anesthetics (for example, benzyl alcohol), isotonizing agents (for example, sodium chloride, mannitol, sorbitol), adsorption inhibitors (for example, Tween 80 or Miglyol 812), solubility enhancing agents (for example, cyclodextrins and derivatives thereof), stabilizers (for example, serum albumin), and reducing agents (for example, glutathione) can be included. When the composition is a liquid, the tonicity of the formulation, as measured with reference to the tonicity of 0.9% (w/v) physiological saline solution taken as unity, is typically adjusted to a value at which no substantial, irreversible tissue damage will be induced at the site of administration. Generally, the tonicity of the solution is adjusted to a value of about 0.3 to about 3.0, such as about 0.5 to about 2.0, or about 0.8 to about 1.7.

For any use, the anti-microbial peptides can be dispersed in a base or vehicle, which can include a compound having a capacity to disperse the compound, and any desired additives. In some embodiments, the base can be selected from a wide range of suitable compounds, including but not limited to, copolymers of polycarboxylic acids or salts thereof, carboxylic anhydrides (for example, maleic anhydride) with other monomers (for example, methyl (meth)acrylate, acrylic acid and the like), hydrophilic vinyl polymers, such as polyvinyl acetate, polyvinyl alcohol, polyvinylpyrrolidone, cellulose derivatives, such as hydroxymethylcellulose, hydroxypropylcellulose and the like, and natural polymers, such as chitosan, collagen, sodium alginate, gelatin, hyaluronic acid, and nontoxic metal salts thereof. Often, a biodegradable polymer is selected as a base or vehicle, for example, polylactic acid, poly (lactic acid-glycolic acid) copolymer, polyhydroxybutyric acid, poly(hydroxybutyric acid-glycolic acid) copolymer and mixtures thereof. Alternatively or additionally, synthetic fatty acid esters such as polyglycerin fatty acid esters, sucrose fatty acid esters and the like can be employed as vehicles. Hydrophilic polymers and other vehicles can be used alone or in combination, and enhanced structural integrity can be imparted to the vehicle by partial crystallization, ionic bonding, cross-linking and the like. The vehicle can be provided in a variety of forms, including fluid or viscous solutions, gels, pastes, powders, microspheres and films for direct application to a mucosal surface.

An anti-microbial peptide can be combined with the base or vehicle according to a variety of methods, and release of the agents can be by diffusion, disintegration of the vehicle, or associated formation of water channels. In some circumstances, an anti-microbial peptide is dispersed in microcapsules (microspheres) or nanocapsules (nanospheres) prepared from a suitable polymer, for example, isobutyl 2-cyanoacrylate (see, for example, Michael et al., *J. Pharmacy Pharmacol.* 43:1-5, 1991), and dispersed in a biocompatible dispersing medium, which yields sustained delivery and biological activity over a protracted time.

Pharmaceutical compositions for administering the agents can also be formulated as a solution, microemulsion, or other ordered structure suitable for high concentration of active ingredients. The vehicle can be a solvent or dispersion medium containing, for example, water, ethanol, polyol (for example, glycerol, propylene glycol, liquid polyethylene glycol, and the like), and suitable mixtures thereof. Proper fluidity for solutions can be maintained, for example, by the use of a coating such as lecithin, by the maintenance of a desired particle size in the case of dispersible formulations, and by the use of surfactants. In many cases, it will be desirable to include isotonic agents, for example, sugars, polyalcohols, such as mannitol and sorbitol, or sodium chloride in the composition. Prolonged absorption of the compound can be brought about by including in the composition an agent which delays absorption, for example, monostearate salts and gelatin.

In certain embodiments, one or more anti-microbial peptides can be administered in a time release formulation, for example in a composition which includes a slow release polymer. These compositions can be prepared with vehicles that will protect against rapid release, for example a controlled release vehicle such as a polymer, microencapsulated delivery system or bioadhesive gel. Prolonged delivery in various compositions of the disclosure can be brought about by including in the composition agents that delay absorption, for example, aluminum monostearate hydrogels and gelatin. When controlled release formulations are desired, controlled release binders suitable for use in accordance with the disclosure include any biocompatible controlled release material which is inert to the active agent and which is capable of incorporating the compound and/or other biologically active agent. Numerous such materials are known in the art. Useful controlled-release binders are materials that are metabolized slowly under physiological conditions following their delivery (for example, at a mucosal surface, or in the presence of bodily fluids). Appropriate binders include, but are not limited to, biocompatible polymers and copolymers well known in the art for use in sustained release formulations. Such biocompatible compounds are non-toxic and inert to surrounding tissues, and do not trigger significant adverse side effects, such as nasal irritation, immune response, inflammation, or the like. They are metabolized into metabolic products that are also biocompatible and easily eliminated from the body.

Exemplary polymeric materials for use include, but are not limited to, polymeric matrices derived from copolymeric and homopolymeric polyesters having hydrolyzable ester linkages. A number of these are known in the art to be biodegradable and to lead to degradation products having no or low toxicity. Exemplary polymers include polyglycolic acids and polylactic acids, poly(DL-lactic acid-co-glycolic acid), poly (D-lactic acid-co-glycolic acid), and poly(L-lactic acid-co-glycolic acid). Other useful biodegradable or bioerodable polymers include, but are not limited to, such polymers as poly(epsilon-caprolactone), poly(epsilon-aprolactone-CO-lactic acid), poly(epsilon.-aprolactone-CO-glycolic acid), poly(beta-hydroxy butyric acid), poly(alkyl-2-cyanoacrilate), hydrogels, such as poly(hydroxyethyl methacrylate), polyamides, poly(amino acids) (for example, L-leucine, glutamic acid, L-aspartic acid and the like), poly(ester urea), poly(2-hydroxyethyl DL-aspartamide), polyacetal polymers, polyorthoesters, polycarbonate, polymaleamides, polysaccharides, and copolymers thereof. Many methods for preparing such formulations are well known to those skilled in the art (see, for example, *Sustained and Controlled Release Drug Delivery Systems*, J. R. Robinson, ed., Marcel Dekker, Inc., New York, 1978). Other useful formulations include controlled-release microcapsules (U.S. Pat. Nos. 4,652,441 and 4,917,893), lactic acid-glycolic acid copolymers useful in making microcapsules and other formulations (U.S. Pat. Nos. 4,677,191 and 4,728,721) and sustained-release compositions for water-soluble peptides (U.S. Pat. No. 4,675,189).

The pharmaceutical compositions typically are sterile and stable under conditions of manufacture, storage and use. Sterile solutions can be prepared by incorporating the anti-microbial peptide in the required amount in an appropriate solvent with one or a combination of ingredients enumerated herein, as required, followed by filtered sterilization. Generally, dispersions are prepared by incorporating the compound and/or other biologically active agent into a sterile vehicle that contains a basic dispersion medium and the required other ingredients from those enumerated herein. In the case of sterile powders, methods of preparation include vacuum drying and freeze-drying which yields a powder of the compound plus any additional desired ingredient from a previously sterile-filtered solution thereof. The composition can include additional anti-bacterial and antifungal agents, for example, parabens, chlorobutanol, phenol, sorbic acid, thimerosal, and the like.

The anti-microbial peptides described herein may be used in combination (e.g., co-administered) with one or more antibiotics and/or one or more antiseptics. Illustrative antibiotics include, for example, tetracycline-derived antibiotics such as, e.g., tetracycline, doxycycline, chlortetracycline, clomocycline, demeclocycline, lymecycline, meclocycline, metacycline, minocycline, oxytetracycline, penimepicycline, rolitetracycline, or tigecycline; amphenicol-derived antibiotics such as, e.g., chloramphenicol, azidamfenicol, thiamphenicol, or florfenicol; macrolide-derived antiobiotics such as, e.g., erythromycin, azithromycin, spiramycin, midecamycin, oleandomycin, roxithromycin, josamycin, troleandomycin, clarithromycin, miocamycin, rokitamycin, dirithromycin, flurithromycin, telithromycin, cethromycin, tulathromycin, carbomycin A, kitasamycin, midecamicine, midecamicine acetate, tylosin (tylocine), or ketolide-derived antiobiotics such as, e.g., telithromycin, or cethromycin; lincosamide-derived antiobiotics such as, e.g., clindamycin, or lincomycin; streptogramin-derived antiobiotics such as, e.g., pristinamycin, or quinupristin/dalfopristin; oxazolidinone-derived antiobiotics such as, e.g., linezolid, or cycloserine; aminoglycoside-derived antiobiotics such as, e.g., streptomycin, neomycin, framycetin, paromomycin, ribostamycin, kanamycin, amikacin, arbekacin, bekanamycin, dibekacin, tobramycin, spectinomycin, hygromycin B, paromomycin, gentamicin, netilmicin, sisomicin, isepamicin, verdamicin, astromicin, rhodostreptomycin, or apramycin; steroid-derived antibiotics such as, e.g., fusidic acid, or sodium fusidate; glycopeptide-derived antiobiotics such as, e.g., vancomycin, oritavancin, televancin, teicoplanin, dalbavancin, ramoplanin, bleomycin, or decaplanin; beta-lactam-derived antiobiotics such as, e.g., amoxicillin, ampicillin, pivampicillin, hetacillin, bacampicillin, metampicillin, talampicillin, epicillin, carbenicillin, carindacillin, ticarcillin, temocillin, azlocillin, piperacillin, mezlocillin, mecillinam, pivmecillinam, sulbenicillin, benzylpenicillin, azidocillin, penamecillin, clometocillin, benzathine benzylpenicillin, procaine benzylpenicillin, phenoxymethylpenicillin, propicillin, benzathine, phenoxymethylpenicillin, pheneticillin, oxacillin, cloxacillin, dicloxacillin, flucloxacillin, meticillin, nafcillin, faropenem, biapenem, doripenem, ertapenem, imipenem, meropenem, panipenem, cefacetrile, cefadroxil, cefalexin, cefaloglycin, cefalonium, cefaloridine, cefalotin, cefapirin, cefatrizine, cefazedone, cefazaflur, cefazolin, cefradine, cefroxadine, ceftezole, cefaclor, cefamandole, cefminox, cefonicid, ceforanide, cefotiam, cefprozil, cefbuperazone, cefuroxime, cefuzonam, cefoxitin, cefotetan, cefmetazole, loracarbef, cefcapene, cefdaloxime, cefdinir, cefditoren, cefetamet, cefixime, cefmenoxime, cefodizime, cefoperazone, cefotaxime, cefpimizole, cefpiramide, cefpodoxime, cefsulodin, ceftazidime, cefteram, ceftibuten, ceftiolene, ceftizoxime, ceftriaxone, flomoxef, latamoxef, cefepime, cefozopran, cefpirome, cefquinome, ceftobiprole, aztreonam, tigemonam, sulbactam, tazobactam, clavulanic acid, ampicillin/sulbactam, sultamicillin, piperacillin/tazobactam, co-amoxiclav, amoxicillin/clavulanic acid, or imipenem/cilastatin; sulfonamide-derived antiobiotics such as, e.g., acetazolamide, benzolamide, bumetanide, celecoxib, chlorthalidone, clopamide, dichlorphenamide, dorzolamide, ethoxzolamide, furosemide, hydrochlorothiazide, indapamide, mafenide, mefruside, metolazone, probenecid, sulfacetamide, sulfadiazine, sulfadimethoxine, sulfadoxine, sulfanilamides, sulfamethoxazole, sulfamethoxypyridazine, sulfasalazine, sultiame, sumatriptan, xipamide, zonisamide, sulfaisodimidine, sulfamethizole, sulfadimidine, sulfapyridine, sulfafurazole, sulfathiazole, sulfathiourea, sulfamoxole, sulfadimethoxine, sulfalene, sulfametomidine, sulfametoxydiazine, sulfaperin, sulfamerazine, sulfaphenazole, or sulfamazone; quinolone-derived antiobiotics such as, e.g., cinoxacin, flumequine, nalidixic acid, oxolinic acid, pipemidic acid, piromidic acid, rosoxacin, ciprofloxacin, enoxacin, fleroxacin, lomefloxacin, nadifloxacin, ofloxacin, norfloxacin, pefloxacin, rufloxacin, balofloxacin, grepafloxacin, levofloxacin, pazufloxacin, sparfloxacin, temafloxacin, tosufloxacin, besifloxacin, clinafloxacin, garenoxacin, gemifloxacin, moxifloxacin, gatifloxacin, sitafloxacin, trovafloxacin, alatrofloxacin, prulifloxacin, danofloxacin, difloxacin, enrofloxacin, ibafloxacin, marbofloxacin, orbifloxacin, pradofloxacin, sarafloxacin, ecinofloxacin, or delafloxacin; imidazole-derived antiobiotics such as, e.g., metronidazole; nitrofuran-derived antiobiotics such as, e.g., nitrofurantoin, or nifurtoinol; aminocoumarin-derived antiobiotics such as, e.g., novobiocin, clorobiocin, or coumermycin A1; ansamycin-derived antiobiotics, including rifamycin-derived antiobiotics such as, e.g., rifampicin (rifampin), rifabutin, rifapentine, or rifaximin; and also further antiobiotics such as, e.g., fosfomycin, bacitracin, colistin, polymyxin B, daptomycin, xibornol, clofoctol, methenamine, mandelic acid, nitroxoline, mupirocin, trimethoprim, brodimoprim, iclaprim, tetroxoprim, or sulfametrole; without being limited thereto.

Illustrative antiseptics include, for example, acridine-derived antiseptics such as, e.g., ethacridine lactate, aminoacridine, or euflavine; amidine-derived or biguanide-derived antiseptics such as, e.g., dibrompropamidine, chlorhexidine, propamidine, hexamidine, or polihexanide; phenol-derived antiseptics such as, e.g., phenol, hexachlorophene, policresulen, triclosan, chloroxylenol, or biphenylol; nitrofuran-derived antiseptics such as, e.g., nitrofurazone; iodine-based antiseptics such as, e.g., iodine/octylphenoxypolyglycolether, povidone-iodine, or diiodohydroxypropane; quinoline-derived antiseptics such as, e.g., dequalinium, chlorquinaldol, oxyquinoline, or clioquinol; quaternary ammonium-derived antiseptics such as, e.g., benzalkonium, cetrimonium, cetylpyridinium, cetrimide, benzoxonium chloride, or didecyldimethylammonium chloride; mercurial antiseptics such as, e.g., mercuric amidochloride, phenylmercuric borate, mercuric chloride, mercurochrome, thiomersal, or mercuric iodide; silver-based antiseptics such as, e.g., silver nitrate; alcoholic antiseptics such as, e.g., propanol (including isopropanol), or ethanol; and also further antiseptics such as, e.g., potassium permanganate, sodium hypochlorite, hydrogen peroxide, eosin, tosylchloramide sodium, dichlorobenzyl alcohol, ambazone, benzethonium, myristylbenzalkonium, hexylresorcinol, or acriflavinium chloride; without being limited thereto.

In some embodiments, one or more anti-microbial peptides are formulated with an additional anti-bacterial agent, such as an antibiotic selected from the group consisting of amikacin, kanamycin, clarithromycin, erythromycin, erythromycin, estolate/ethylsuccinate/gluceptatellactobionate/stearate, penicillin G, penicillin V, methicillin, cloxacillin, dicloxacillin, ampicillin, amoxicillin, ticarcillin, carbenicillin, mezlocillin, azlocillin, piperacillin, cephalothin, cefazolin, cefaclor, cefonicid, cefmetazole, cefotetan, cefprozil, loracarbef, cefetamet, cefoperazone, ceftizoxime, ceftazidime, ceftobiprole, cefepime, cefixime, cefpirome, cefpodoxime, cefsulodin, meropenem, imipenem, doripenem, aztreonam, fleroxacin, nalidixic acid, norfloxacin, ciprofloxacin, ofloxacin, enoxacin, lomefloxacin, cinoxacin, doxycycline, minocycline, tetracycline, polymyxin B, or colistin.

Co-therapy using the agents disclosed herein with other antibiotic(s) and/or antiseptic(s) may result in a synergistic effect, i.e. the agents acting together may create an effect greater than that predicted by knowing only the separate effects of the individual agents. Such a synergistic effect might be particularly advantageous if lesser amounts of the agent(s), antibiotic(s) and/or antiseptic(s) may then be used.

Thus, possible side-effects of the compound(s), antibiotic(s) and/or antiseptic(s) might be diminished or avoided.

Treatment of a Biofilm

Disclosed herein is a method for treating an *E. coli* or *P. aeruginosa* biofilm. In a one embodiment, a surface infected with a biofilm is selected for treatment. In one embodiment, the method involves contacting a biofilm with an effective amount of the disclosed anti-microbial peptide that has an anti-bacterial activity against the biofilm, thereby treating the biofilm. In one embodiment of the method, contacting a biofilm involves contacting a mass, aggregation, or community of *E. coli* or *P. aeruginosa* attached to a surface and the associated extracellular substances produced by the bacteria. In another embodiment, the method involves contacting *E. coli* or *P. aeruginosa*, such as a culture, with an effective amount of the anti-microbial peptide.

In one embodiment, an anti-microbial activity is an increase in cell lysis. Thus, in one embodiment of the method, contacting the biofilm of *E. coli* or *P. aeruginosa* with the anti-microbial peptide or a variant thereof, increases bacterial cell lysis in the biofilm, or increases lysis of *E. coli* or *P. aeruginosa* compared to a biofilm in the absence of the peptide. In particular embodiments, an increase in bacterial cell lysis is at least a 2%, at least a 5%, at least a 10%, at least a 20%, at least a 30%, at least a 40%, at least a 50%, at least a 75%, at least a 100%, at least a 150%, at least a 200% or more increase in lysed cells in the biofilm. In another embodiment, an anti-bacterial activity is a reduction in biofilm cell viability. In particular embodiments, a reduction in cell viability is a reduction of viable cells by at least 25%, at least 50%, at least 75%, at least 80%, at least 90%, at least 95%, at least 96%, at least 97%, at least 98%, at least 99%, or 100%. In one specific non-limiting example, the anti-bacterial activity of the peptide, or a variant thereof, can be measured by the production or the size of a clear zone on a microbial lawn surrounding a bacterial colony, or by measuring the clarity of a culture. However, the anti-microbial activity can also be measured by measuring intracellular ATP, membrane depolarization or membrane permeabilization of *E. coli* or *P. aeruginosa*.

In some embodiments of the method, the biofilm is attached to a living or non-living surface. In other particular embodiments, a non-living surface in the subject is a surface of a medical device, such as the surface of an indwelling medical device. Examples of indwelling medical devices include intravascular catheters (for example, intravenous and intra-arterial), right heart flow-directed catheters, Hickman catheters, arteriovenous fistulae, catheters used in hemodialysis and peritoneal dialysis (for example, silastic, central venous, Tenckhoff, and Teflon catheters), vascular access ports, indwelling urinary catheters, urinary catheters, silicone catheters, ventricular catheters, synthetic vascular prostheses (for example, aortofemoral and femoropopliteal), prosthetic heart valves, prosthetic joints (for example, prosthetic knee or hip joints), orthopedic implants, penile implants, shunts (for example, Scribner, Torkildsen, central nervous system, portasystemic, ventricular, ventriculoperitoneal), intrauterine devices, dental prostheses (for example, permanent dentures or partial implants), stents (for example, ureteral stents), artificial voice prostheses, tympanostomy tubes, gastric feeding tubes, endotracheal tubes, pacemakers, implantable defibrillators, tubing, cannulas, probes, blood monitoring devices, needles, mouth guards, night guards, dentures, orthodontic retainers, contact lenses, and the like. However, the medical device need not be implantable, nor need it have direct therapeutic activity. The device can be, for example, a storage device, such as a medical storage device, for example a contact lens case.

In particular embodiments, the indwelling medical devices include surgically implantable devices (for example, a pacemaker, prosthetic heart valves, shunts, prosthetic joints, orthopedic implants, dental implants or synthetic vascular prostheses). In other particular embodiments, the indwelling medical device is not surgically implanted, but is routinely inserted and removed by the subject (for example, a mouth guard, a night guard, removable dentures, an orthodontic retainer, or a contact lens). In some embodiments, the medical device has a lumen (for example, a catheter).

In one embodiment of the method, the medical device is suitable for surgical implantation within the body of the subject. In another embodiment of the method, the medical device is surgically implanted within the body of the subject. In a further embodiment, the medical device is non-permanently inserted in the subject. In yet a further embodiment, the medical device is not introduced, inserted, or surgically implanted in the subject.

In other embodiments, the surface to be treated is a non-living surface of an object that is not an indwelling medical device (a surface that is external to the subject). In particular embodiments, the non-living surface is on or near a food preparation area (for example, a counter, a table, or a floor), on food preparation utensils (for example, a knife), on a household surface (for example, a shower or a toilet), or a fluid-conducting or gas-conducting object having a lumen (such as a water, oil, gas, or sewage pipe, or tubing). The agents and compositions disclosed herein may also be used for removing or reducing or preventing bacterial contamination of a substrate such as food processing equipment, food processing plants, surfaces coming into contact with foodstuff, and surfaces in hospitals and surgeries.

In some embodiments, the anti-microbial peptide is administered to the surface before a biofilm is formed in order to inhibit the formation of a biofilm on the surface. Alternatively, at the first indication of biofilm formation, the methods may be used to inhibit further biofilm formation (or growth or multiplication). This can be achieved by contacting the surface with the peptide such that the anti-microbial peptide adheres to the surface. Suitable coatings for indwelling medical devices include various hydrogel coatings. The disclosed anti-microbial peptide can be incorporated into the hydrogel before or after the hydrogel is applied to the medical device. In some embodiments, the hydrogel coating of the medical device includes an additional anti-microbial agent, such as an antibiotic (see above), a bacteriocin, an anti-microbial peptide, or a bacteriophage.

The surfaces can have surfaces composed of thermoplastic or polymeric materials such as polyethylene, Dacron, nylon, polyesters, polytetrafluoroethylene, polyurethane, latex, silicone elastomers, and the like. The surfaces may be smooth or rough, for example, a smooth polymeric surface of a catheter lumen or a relatively rough Dacron patch for repairing an abdominal or vascular defect. Metallic surfaces are also amenable to treatment with the disclosed compositions.

Various methods can be employed to treat the surfaces with the disclosed anti-microbial peptide. The disclosed anti-microbial peptide, or a variant thereof, may be applied to (for example, a composition comprising the anti-microbial peptide, or a variant thereof, may be painted, sprayed, or soaked on) the living or non-living surface. In particular embodiments, the surface is dipped or immersed in a composition comprising the anti-microbial peptide. One specific, non-limiting example of the method is to flush the lumen of a medical device with a composition containing the disclosed anti-microbial peptide. In particular embodiments of the methods, the flushing solution is composed of sterile media or sterile normal saline solutions in addition to the anti-microbial peptide. In some embodiments of the method, the medical device is removed from the subject prior to treatment. In other embodiments of the method, the subject is administered the disclosed anti-microbial peptide. Without being bound by theory, the disclosed methods improve the operability or reduce the infectious potential of a medical device, or reduce the occlusion of a pipe or tubing, caused by the growth or encrustation of the biofilm on the surface.

In further embodiments, an additional agent used is to facilitate removing the E. coli or P. aeruginosa biofilm deposited on a surface. For example, the compositions can include a surfactant or an anti-bacterial enzyme, or combinations thereof. Exemplary surfactants include, but are not limited to, biosurfactants (such as glycolipids, lipopeptides, depsipeptides, phospholipids, substituted fatty acids, lipopolysaccharides, surlactin, surfactin, visconsin, and rhamnolipids), sodium dodecyl sulfate, quaternary ammonium compounds, alkyl pyridinium iodides, Tween 80, Tween, 85, Triton X-100, hexadecyl pyridinium chloride, polysorbates, sorbitans, poly(oxyethylene) alkyl ethers, poly(oxyethylene) alkyl esters, and the like. Exemplary anti-bacterial enzymes are, but not limited to, a lytic enzyme, an acylase, an aminopeptidase, an amylase, a carbohydrase, a carboxypeptidase, a catalase, a cellulase, a chitinase, a cutinase, a cyclodextrin glycosyltransferase, a deoxyribonuclease, an esterase, an alpha-galactosidase, a beta-galactosidase, a glucoamylase, an alpha-glucosidase, a beta-glucosidase, a haloperoxidase, an invertase, a laccase, a lipase, a mannosidase, an oxidase, a pectinolytic enzyme, a peptidoglutaminase, a peroxidase, a phytase, a polyphenoloxidase, a proteolytic enzyme, a ribonuclease, a transglutaminase, a xylanase, and lysostaphin.

The disclosure is illustrated by the following non-limiting Examples.

EXAMPLES

Emergence of antibiotic resistant strains due to widespread use of antibiotics and dearth of new antibiotics has resulted in looking for new anti-microbial agents with new targets and unique mechanism of action. Anti-microbial peptides (AMPs) are gaining importance due to their superior and dynamic mechanism of action compared to antibiotics (Hancock, R. E. (1997) *Lancet* 349, 418-422). AMPs have existed for millions of years; however resistance to anti-microbial peptides has not been reported. Computer-assisted peptide design, combinatorial libraries and structure based designs are some of the methods used for designing novel AMPs (Tachi, T., et al., (2002) *Biochemistry* 41, 10723-10731). Another way to develop novel anti-microbial peptides is by using recombinant bacteriophages engineered to display short random peptide coding sequences in their genome.

Recently, scientists have focused their research on screening novel AMPs by using combinatorial libraries and computational approaches for anti-microbial drug discovery and design (Hancock et al, (1995) *Adv. Microb. Physiol* 37, 135-175; Hadley, E. B. and Hancock, R. E. (2010) *Curr. Top. Med. Chem.* 10, 1872-1881; Loose et al., (2006) *Nature* 443, 867-869; Rathinakumar et al., (2009) *J. Am. Chem. Soc.* 131, 7609-7617; Rathinakumar, R. and Wimley, W. C. (2010) *FASEB J.* 24, 3232-3238; Wang, G., Li, X., and Wang, Z. (2009) *Nucleic Acids Res.* 37, D933-D937). Combinatorial phage-display is a powerful tool for the selection of short peptides binding to any target, biological or non-biological (Adey et al., (1995) *Gene* 156, 27-31; 40,41; Sergeeva et al., (2006) *Adv. Drug Deliv. Rev.* 58, 1622-1654).

Phage-display has been used successfully in a number of applications, including vaccine development, protein drug discovery, and to generate diagnostic and therapeutic peptides (Fang, Z. D. et al., (2006) *Proc. Natl. Acad. Sci. U. S. A* 103, 18444-18449; Kay, B. et al., (2001) *Methods* 24, 240-246; Kay, B. K. and Castagnoli, L. (2003) *Curr. Protoc. Cell Biol. Chapter* 17, Unit 17.4; Sainath et al., (2010) *Biochem. Biophys. Res. Commun.* 395, 93-98; Sergeeva et al., (2006) *Adv. Drug Deliv. Rev.* 58, 1622-1654; Bishop-Hurley, S. L., et al. (2002) *Appl. Environ. Microbiol.* 68, 3315-3320; Bishop-Hurley, S. L., et al., (2005) *Antimicrob. Agents Chemother.* 49, 2972-2978; Bishop-Hurley, S. L., et al. (2010) *Protein Eng Des Sel* 23, 751-757; Knurr, J., et al., (2003) *Appl. Environ. Microbiol.* 69, 6841-6847). Phage-display serves as a valuable tool for the selection of peptides binding to surface epitopes on whole cells (Devlin, J. J., et al., (1990) *Science* 249, 404-406; Fang., Z. D. et al., (2006) *Proc. Natl. Acad. Sci. U. S. A* 103, 18444-18449; Kay, B. K., et al., (2001) *Methods* 24, 240-246; Kay, B. K. and Castagnoli, L. (2003) *Curr. Protoc. Cell Biol.* Chapter 17, Unit 17.4).

Disclosed herein are experiments wherein a 12-mer phage-display library was used to identify peptides binding to the whole cell surface of *E. coli*. Novel peptides that demonstrated binding to *E. coli* cells were identified. The lead peptide, EC5, showed anti-microbial features against Gram-negative organisms and showed significant bactericidal activity against *E. coli* and *P. aeruginosa*. This peptide was then used to design additional peptides with the desired characteristics. These peptides function as new anti-bacterial and anti-viral agents.

Example 1

Materials and Methods

Bacterial Culture and Reagents

All bacterial strains used in this study originated from ATCC (Manassas, Va.): *S. aureus* (ATCC 25923; ATCC 35548), *S. epidermidis* (ATCC 35983), *E. coli* (ATCC 700928; ATCC 25922), *P. aeruginosa* (ATCC 27853; ATCC 12121), *K pneumoniae* (ATCC 10031; ATCC 13885) and *B. cereus* (ATCC 11778). Cultures were maintained and subcultured periodically on nutrient agar plates and stored at 4 to 8° C. until tested. Stock cultures of all bacteria were stored in tryptic soy broth with 10% glycerol at −70° C. Log-phase cultures of bacteria grown in Miller's Luria-Bertani (LB) broth (Mediatech Inc, Herndon, Va.) were concentrated by centrifugation at 3000×g and dilutions were prepared with phosphate-buffered saline (PBS; pH 7.4) (Mediatech Inc, Herndon, Va.). In all experiments bacterial titers were estimated by optical density and confirmed by quantitative culture by plating on nutrient agar (NA) plates.

Biopanning of Phages Binding to *E. coli*

Phage library displaying 12-mer random peptides fused to pIII coat protein (New England Biolabs Ipswich, Mass.) was used for this study. Biopanning and amplification of the phages was performed as described earlier with some modifications (Sainath et al., (2010) *Biochem. Biophys. Res. Commun.* 395, 93-98). In brief, the phage library was depleted of clones binding to *S. aureus* ATCC 25923. For the first round of panning, 96-well plates were coated with whole cells of *E. coli* ATCC 700928 resuspended in PBS pH 7.4 and exposed to the phage library diluted in TBST at a final concentration of $2\times10^{10}$ (100 µl/well). Unbound phages were removed by washing 10 times with TBST. Subsequently bound phages were eluted by adding 100 µl elution buffer (100 mM HCl) for 5 min at room temperature. The eluate containing the bound phage neutralized with 1M Tris (pH 8.0) was collected. The titer of the phage was determined by plating them on LB X-gal/IPTG plates and the phages were amplified in *E. coli* ER2738 and purified with polyethylene-glycol precipitation. In each round of panning, the titer of the phages in washing buffer and that in the elution buffer was determined, and their ratio was analyzed to evaluate the enrichment efficiency.

DNA Sequencing and Peptide Synthesis

Phages from sixth round of biopanning were used for preparing phage stocks to isolate phage genomic DNA for nucleotide sequencing. The DNA sequences were translated into amino acids by using 'Gene Runner' software (generunner.net). Phage peptides were aligned using CLUSTAL® W multiple sequence alignment program (ebi.ac.uk/Tools/msa/clustalw2/) (Higgins, D. G., et al., (1996) *Methods Enzymol.* 266, 383-402; Thompson, J. D. et al., (1994) *Nucleic Acids Res.* 22, 4673-4680). Peptides were synthesized and then biotinylated with a C6-linker and purified by high-pressure liquid chromatography (HPLC).

Assays for Detection of Peptide Binding to *E. coli* Cells

ELISA. Log-phase cultures of bacteria were centrifuged at 3,000×g. The cell pellet was resuspended and 10-fold serial dilutions were made in 1×PBS. Bacterial cell suspension at a concentration of $10^3$ CFU was coated to the wells of 96-well micro plate (Becton Dickinson, Bedford, Mass.) and incubated overnight at RT. Subsequently, cells were fixed in ethanol (Aldrich Chemical Company, Milwaukee, Wis.) for 10 minutes (min) and the plates were air-dried. Wells were blocked with 5% bovine serum albumin (BSA) (Sigma, St. Louis, Mo.) for 60 min at room temperature (RT), rinsed with PBS and then EC5 peptide suspended in phosphate buffered saline (PBS) at a final concentration of 50 µg/ml were added to all the wells and incubated for 15 min. Following incubation, wells were washed 3 times with PBST buffer (PBS pH 7.4, 0.01% Tween 20). The wells were further incubated with 1:10,000 dilution of streptavidin-HRP conjugate (Upstate, Temecula, Calif.) for 15 min and washed with PBST buffer. Tetramethylbenzidine (TMB) membrane peroxidase substrate (Zymed Laboratories, Carlsbad, Calif.) system was used to detect the enzyme label in accordance with the manufacturer's instructions. The color development in the 96-well plate was recorded by using SYNERGY 4™ BioTek micro plate reader (BioTek Instruments, Winooski, Vt.) at 490 nm wavelength.

Fluorometry Using Qdot Nanocrystals

The assay was carried out as described earlier (21,24). Bacterial cell suspensions at a concentration of $10^3$ CFU were incubated with EC5 (50 µg/ml) in an eppendorf tube at room temperature for 60 min. Following three washes with 1×PBS pH 7.4 the pellet was resuspended in 1000 of 1:10,000 dilution of streptavidin-conjugated Q dots (QD 605) solution (Invitrogen, Gaithersburg, Md.). The fluorometric counts were measured using SYNERGY 4™ BioTek micro plate reader (BioTek Instruments, Winooski, Vt.).

Bioinformatic Tools for Peptide Characterization

Physicochemical properties of the peptide (Molecular weight and pI) were predicted using the Compute pI/Mw tool expasy server (web.expasy.org/compute_pi/). Hydrophobicity and net charge of the peptides were predicted using Antimicrobial peptide database server (aps.unmc.edu/AP/prediction/prediction_main.php) (Wang, G., Li, X., and Wang, Z. (2009) *Nucleic Acids Res.* 37, D933-D937). Homology modelling was done using the (PS) 2v2: Protein Structure Prediction Server (Chen, C. C., (2009) *BMC. Bioinformatics.* 10, 366). (PS) 2 is an automated server that builds 3D models using the package MODELLER.

Evaluation of Bactericidal Activity of the EC5 Peptide

In vitro anti-bacterial activity of EC5. The test microorganisms mentioned earlier in the experimental procedures were used to evaluate the bactericidal activity of EC5 peptide. The minimum inhibitory concentrations (MICs) of the peptide were determined by standard dilution assay as recommended by Clinical and Laboratory Standard Institutes (CLSI) guidelines (Azad, M. A., et al., (2011) *Antimicrob. Agents Chemother.* 55, 2137-2145). Bacteria were grown to mid-logarithmic phase in cation-supplemented Mueller-Hinton broth (MHB) (Becton Dickinson, Sparks, Md.) on an orbital shaker (37° C.) and diluted to a 0.5 McFarland standard to a final volume of 1 ml. Decreasing concentrations of the peptide were incubated with the microorganisms. Results were recorded by visual inspection after 24 h of incubation at 37° C. Assay was repeated three separate times to ensure reproducibility. Since EC5 exhibited anti-bacterial activity against *E. coli* and *P. aeruginosa*, time-kill kinetics of the *E. coli* and *P. aeruginosa* strains were examined. EC5 concentrations 0x, 0.5x, 1x, and 2×MIC were incubated with logarithmic phase of bacteria of approximately $10^5$ CFU/ml in an orbital shaker for 48 h at 37° C. Samples were drawn and plated on NA plates. Polymyxin B was used as a positive control and peptide with no anti-bacterial activity from our previous studies was used as a negative control.

Anti-Bacterial Activity in Blood Matrices

The anti-bacterial activity of the peptide in the presence of homologous plasma and platelets were assessed. Platelet Concentrates (PCs) in bags were obtained and stored at room temperature as described earlier (Mohan, K. V. et al., (2010) *Transfusion* 50, 166-173). Plasma was isolated from the PC bag by collecting 25 ml of PCs and subjecting the sample to a low speed centrifugation step to separate PLT-rich plasma from plasma. For assays log phase cultures of bacteria grown in Luria-Bertani (LB) broth were centrifuged at 3000×g and suspended in 1×PBS pH7.4. Bacterial titers were estimated by measuring the optical density (OD) and microscopy. Approximately $10^5$ CFU/ml of each bacterial strain was spiked into 0.1 ml of plasma or platelets and incubated with peptide at concentrations ranging from 50 to 0 µg/ml. Incubation was carried out at room temperature for 2 h on a shaker. At the end of 2-h exposure period, a fixed volume of the suspension was plated on NA plates, and incubating at 37° C. for 18 to 24 h. Bactericidal activity was measured by log-reduction by viable bacteria.

Measurement of Hemolytic Activity

The ability of EC5 to induce hemolysis of chicken red blood cells (ch-RBCs) was assessed as previously described (Pathak, S. and Chauhan, V. S. (2011) *Antimicrob. Agents Chemother.* 55, 2178-2188). Red blood cells were harvested and washed with phosphate-buffered saline (PBS). 1% (vol/vol) suspension was made with PBS. 100 µl and 50 µl of this RBC suspension were transferred to 96-well microtiter plates. Two-fold serial dilutions of the peptide samples were prepared and added to the RBCs. The reaction mixture was incubated at 37° C. for 24 h in microtiter plates. Results were visually determined.

Toxicity of Peptide for Eukaryotic Cells

Toxicity of EC5 towards MDCK (Madin Darby Canine Kidney ATCC CCL-34) cells and Vero cells (ATCC CC1-81) was tested by PRESTOBLUE™ Cell Viability assay (Invitrogen, Carlsbad, Calif.) according to the manufacturer's protocol. Briefly MDCK and Vero cells were cultured in Eagle's Minimum Essential Medium (EMEM) (Invitrogen, Carlsbad, Calif.) and Dulbecco's modification of Eagle medium respectively. The medium was supplemented with 10% fetal bovine serum, 2 mM glutamine, 100 units/ml of penicillin and 100 units/ml streptomycin and was plated in wells. Peptides were added at various concentrations and incubated overnight with the cells at 37° C. in a 5% $CO_2$ atmosphere. PRESTO-BLUE™ Cell Viability reagent was added and the fluorescence read using SYNERGY 4™ BioTek micro plate reader (BioTek Instruments, Winooski, Vt.).

Outer Membrane Permeabilization Assay

Membrane-permeabilizing activity of the peptide was determined using the fluorescent dye N-phenyl-1-napthylamine (NPN) assay, as described earlier (Loh et al. (1984) *Antimicrob. Agents Chemother.* 26, 546-551), with intact cells of *E. coli* and *P. aeruginosa*. The increase in fluorescence due to partitioning of NPN uptake into outer membrane (OM) was measured by addition of increasing concentrations of peptide. Polymyxin B (PMB) was taken as a positive control due to its outer membrane permeabilizing properties. All experiments were performed three times. *S. aureus* was used as a negative control.

Membrane Permeability as Assessed by Propidium Iodide (PI) and SYTO9 Uptake-Based Assay The effects of EC5 on the membrane integrity of *E. coli* and *P. aeruginosa* cells were assessed using the LIVE/DEAD BACLIGHT™ kit (Invitrogen, Oregon) according to the manufacturer's protocol. Membrane integrity of the cells after the addition of different concentrations of peptide EC5 was measured using fluorescence micro plate reader (BioTek Instruments, Winooski, Vt.). Experiments were done in triplicates. PMB was used as a positive control.

Membrane Depolarization Assay ($\Delta\psi$)

Membrane depolarization activity ($\Delta\psi$) of the peptide was determined with intact *E. coli* and *P. aeruginosa* cells and the membrane potential-sensitive fluorescent dye, 3,3'-dipropylthiadicarbocyanine Iodide (diSC (3)5) (Invitrogen, Oregon), according to described methods (Sims, P. J., et al (1974) *Biochemistry* 13, 3315-3330). Briefly, bacterial cells of mid-logarithmic phase were harvested by centrifugation and washed twice with HEPES buffer (5 mM HEPES, 5 mM glucose, pH 7.6). The cells were suspended in the same buffer to an OD of 0.05. The cell suspension was incubated with 0.4 mM diSC (3)5 until maximal uptake of the dye. 100 mM KCl was added to equilibrate the cytoplasmic and external potassium ion concentration of peptide, and fluorescence was monitored at an excitation wavelength of 622 nm and an emission wavelength of 670 nm. Polymyxin B was used as a positive control and *S. aureus* cells were used as negative control. Simultaneously the cells were plated on NA plates and incubated at 37° C. overnight to assess the number of CFU.

Determination of ATP Inhibition

The effects of EC5 on ATP inhibition as a measure of metabolic activity of *E. coli* and *P. aeruginosa* cells was determined by using BACTITER-GLO™ assay kit (Promega) according to the manufacturer's protocol. The luminescent signal correlates with the number of viable microbial cells based on the amount of ATP present after the addition of different concentrations of the peptide. Polymyxin B was included as a positive control.

Molecular Dynamic Simulations

In-silico docking studies of EC5 with lipid bilayers were conducted using Cluspro 2.0 version software (Comeau, S. R., (2004) *Nucleic Acids Res.* 32, W96-W99) and Hex protein docking (Macindoe, G., et al., (2010) *Nucleic Acids Res.* 38, W445-W449). Files for POPE (1-palmitoyl-2-oleoyl-phosphoethanolamine) were accessed from Tieleman website (moose.bio.ucalgary.ca) as described (Yount, N. Y., et al., (2011) *PLoS. One.* 6, e26727). Structural files for EC5 were downloaded in PDB file format from (PS) 2v2: Protein Structure Prediction Server. Models of interaction of EC5 with lipid bilayers were generated by the Hex docking server (hex-server.loria.fr/) and Cluspro protein-protein docking server (Version 2.0). The rigid body docking is performed, using ZDOCK based on the fast Fourier transform correlation techniques. The scoring function of ZDOCK is based on shape complementarities, electrostatic potentials and desolvation terms. Filtering is performed using pair wise root mean square deviation clustering and empirical free energy functions. The ligand is minimized by the CHARMM algorithm in the presence of receptor. The 3D Model structures were visualized using PYMOL (version 0.99; http://www.pymol.org).

Statistical Analyses

Assays described here were performed at least three independent times. Mean values ±SD (Standard Deviation) was calculated using GraphPad prism 5. Values were considered significant when p<0.05.

Example 2

Phage-Display Selection of Peptides Binding to *E. coli*

A 12-mer random phage display library was used to affinity select for peptides binding to the cell surface of *E. coli*. In order to eliminate non-specific binding phages and to select peptides that bind specifically to *E. coli*, a subtractive phage-display approach was used where the library was first pre-adsorbed against *S. aureus* ATCC 25923 to eliminate phages binding to the Gram-positive cell surface. The remaining phage library was then used to affinity select for peptides binding to whole cell surface of *E. coli* ATCC 700928. Six rounds of biopanning were performed and the enrichment level was determined prior to amplification by *E. coli* ER2738 infection. Enrichment level was monitored after each round by determining the titer of eluted phages. There was an increase in recovery rate after each round of selection indicating effective enrichment of the phage clones. After six rounds of biopanning, individual phage clones were isolated from which genomic DNA was extracted and sequenced. Five of the clones encoded the same peptide sequence RLL-FRKIRRLKR, hereafter referred as EC5. Remaining clones encoded unique peptide sequences (Table 1). The amino acid sequences of the clones were aligned using ClustalW.

TABLE 1

Deduced amino acid sequences of the phage-displayed peptides

| Clone | Frequency | Amino acid sequence |
|---|---|---|
| EC2 | 1/10 | SGHQLLLNKMPN |
| EC5 | 5/10 | RLLFRKIRRLKR |
| EC6 | 1/10 | MDMRTTDIRDTS |
| EC8 | 1/10 | RNHPATLTGTGG |
| EC9 | 1/10 | GILSELGKALGG |
| EC10 | 1/10 | GAPALSTPPLSR |

EC2 is SEQ ID NO: 4; EC5 is SEQ ID NO: 1, wherein $X_1$ is R; $X_2$ is L; $X_3$ is R; $X_4$ is K; $X_5$ is I; $X_6$ is R; $X_7$ is R; $X_8$ is L; and $X_9$ is K and $X_{10}$ is R; EC6 is SEQ ID NO: 5; EC8 is SEQ ID NO: 6, EC9 is SEQ ID NO: 7; EC10 is SEQ ID NO: 8.

Example 3

EC5 Binds to *E. coli* and *P. aeruginosa*

The binding ability and specificity of the peptide was assessed against a panel of bacteria using ELISA and Fluorometry using Q-dots.

Binding affinities and specificity of the synthesized peptide was analyzed by whole-cell ELISA. The peptide showed significant binding efficiency to *E. coli* cells (p<0.001) as seen in the FIG. 1A. Interestingly the peptide also showed binding to *P. aeruginosa* cells (p<0.05). However, EC5 did not bind to the Gram-positive *S. aureus, S. epidermidis, B. cereus* and to the Gram-negative *K pneumoniae*.

Example 4

Qdot-Based Fluorometry as a Confirmatory Assay for the Binding of EC5 to *E. coli*

Figure 1B:
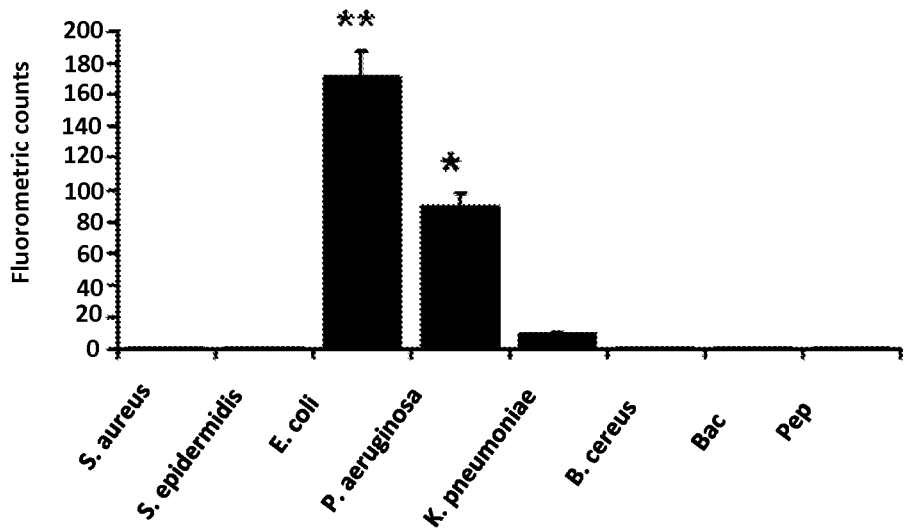

Binding of the peptide to the bacteria was detected using Qdot-nanocrystal cores conjugated to streptavidin. Analysis of the bacterial suspension binding to the peptide was performed in a micro-well plate using a fluorescence plate reader (SYNERGY 4™, Biotek, USA). Excitation was set to a spectral range of 360-485 nm and emission was at 605 nm. Fluorometric analysis revealed that in this experimental setting EC5 was able to bind to *E. coli* as indicated by the significantly higher level of fluorometric counts (p<0.0001) (FIG. 1B). The analysis also confirmed that EC5 binds to *P. aeruginosa* cells.

Example 5

Peptide EC5 Shows Features of Anti-Microbial Peptide

Figure 2A:
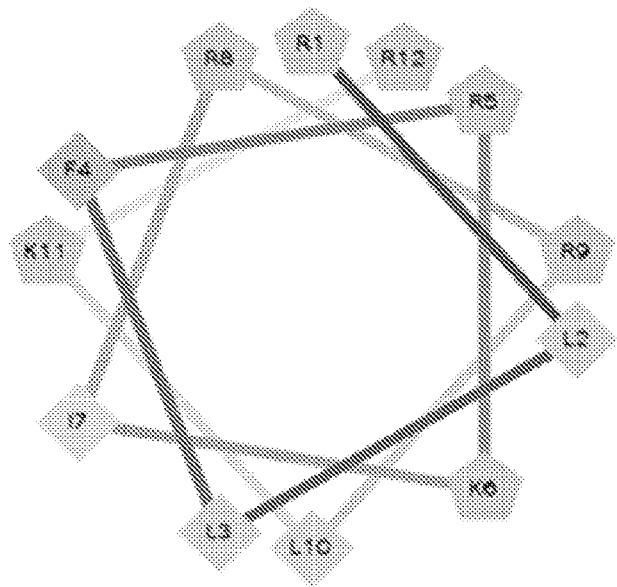
FIGS. 2A-2B. Structure and properties of EC5. A. Edmundson helical wheel presentation of 12-mer EC5. Hydrophobic residues are represented by diamonds and positive charge as pentagons. The most hydrophobic residue is darker grey, with the amount of color decreasing proportionally to the hydrophobicity with least hydrophobic being light grey. B. Ribbon and surface representation of EC5. Ribbon model shows α-helical peptide as the conformation. Secondary structure of the peptide was determined and viewed using PYMOLv0.99
Figure 2B:
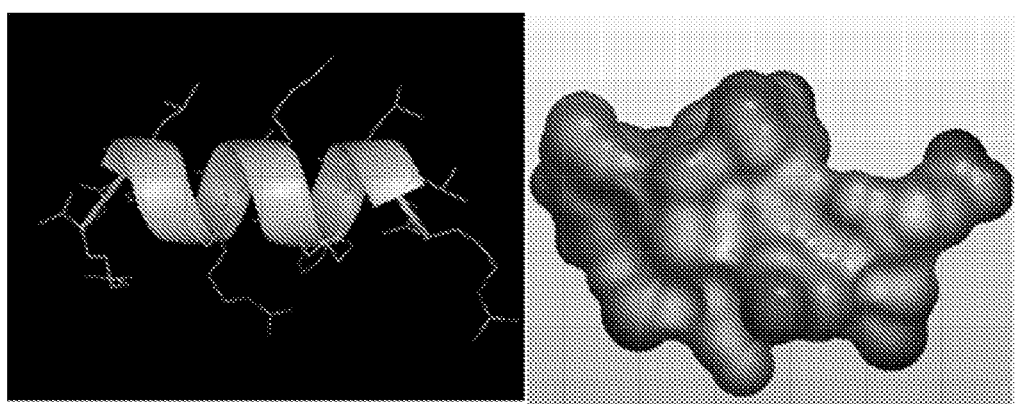

The peptide EC5 exhibited some properties of anti-microbial peptides: cationic with a net positive charge (+7) and a total hydrophobic ratio of 41% (aps.unmc.edu/AP/prediction/prediction_main.php) (Table 2) (Wang, G., Li, X., and Wang, Z. (2009) *Nucleic Acids Res.* 37, D933-D937). By using feature selection method and sequence alignment as a method for prediction of anti-microbial peptide, it was found that EC5 may exhibit anti-microbial properties (amp.biosino.org/) (Wang,. P., et al., (2011) *PLoS. One.* 6, e18476). The peptide showed no significant similarity to other sequences in the Anti-microbial Peptide Database. Secondary structure of EC5 was determined and shown to have α-helix conformation (FIG. 2) with a molecular formula of $C_{75}H_{139}N_{29}O_{13}$. Helical wheel presentation of the peptide was illustrated using the program: (rzlab.ucr.edu/scripts/wheel/wheel.cgi).

Figure 3:
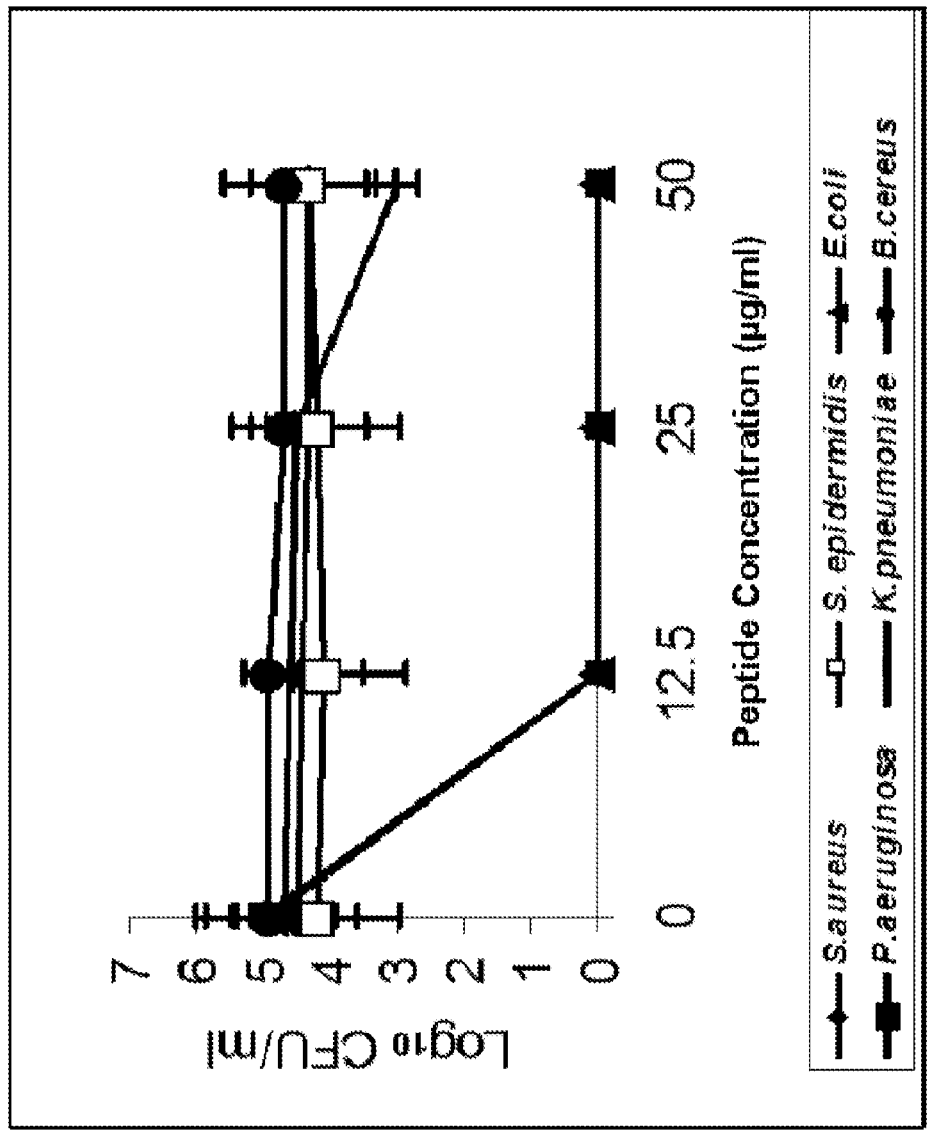
FIG. 3. Effects of EC5 on the growth of different bacteria. Different concentrations of peptide EC5 was added to log-phase cultures of bacteria and their growth monitored after 2 hours (h). Numbers indicate reduction in $\log_{in}$ CFU/ml.
Figure 4A:
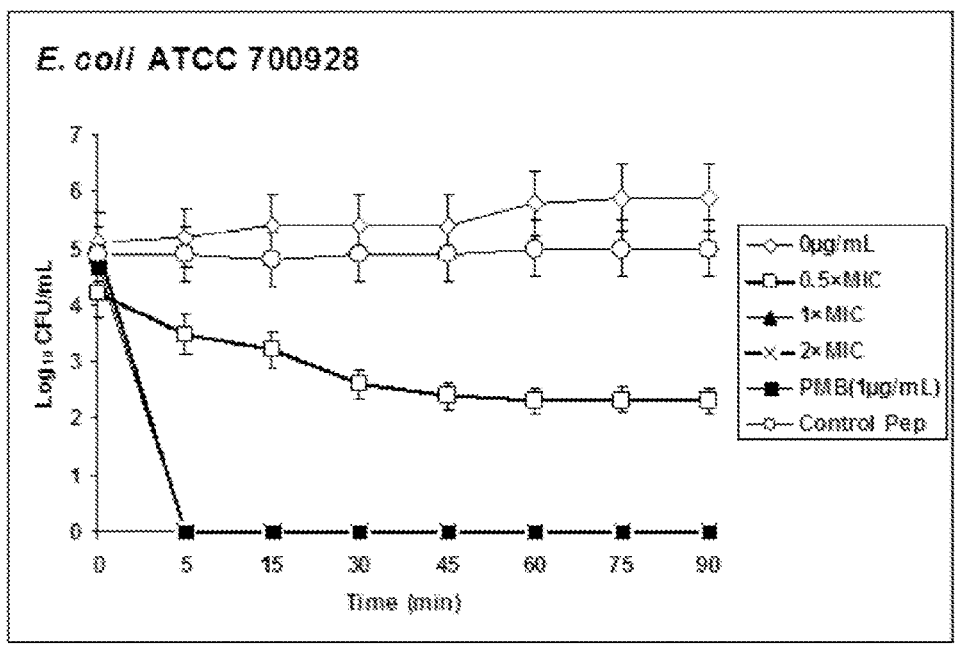
FIGS. 4A-4D. Killing kinetics of A, E. coli ATCC 700928, B, E. coli ATCC 25922, C, P. aeruginosa, ATCC 12121, D, P. aeruginosa ATCC 27853 treated with different concentrations of EC5. The curve represents surviving cell concentrations plotted against time.
Figure 4B:
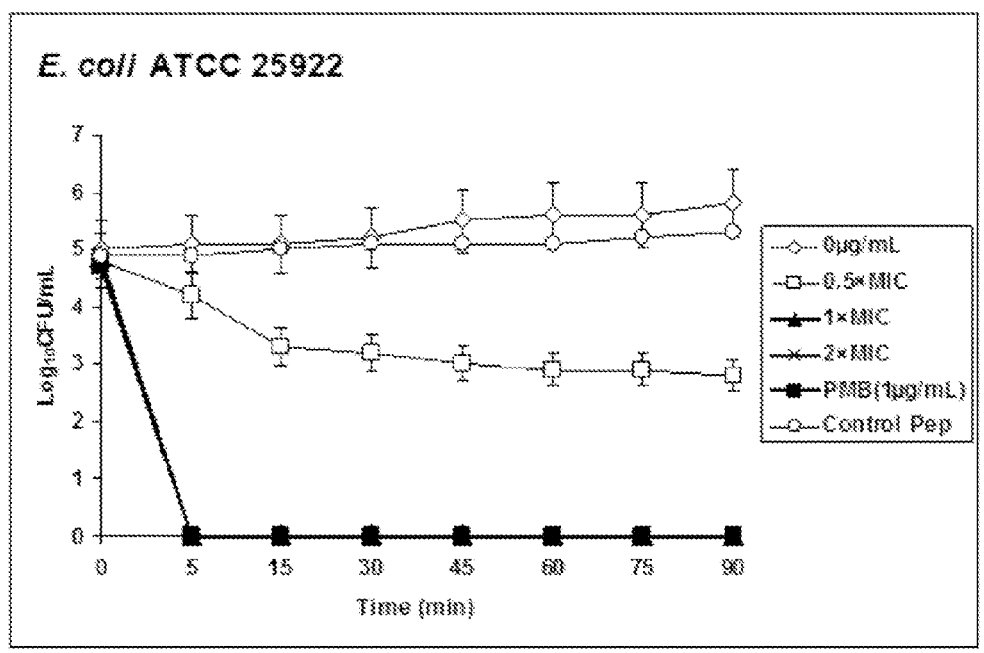
Figure 4C:
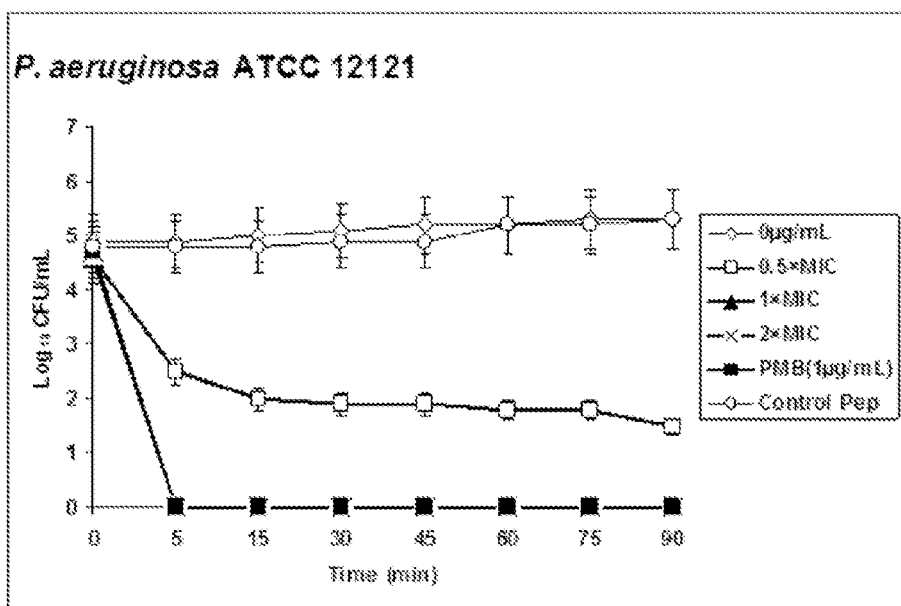
Figure 4D:
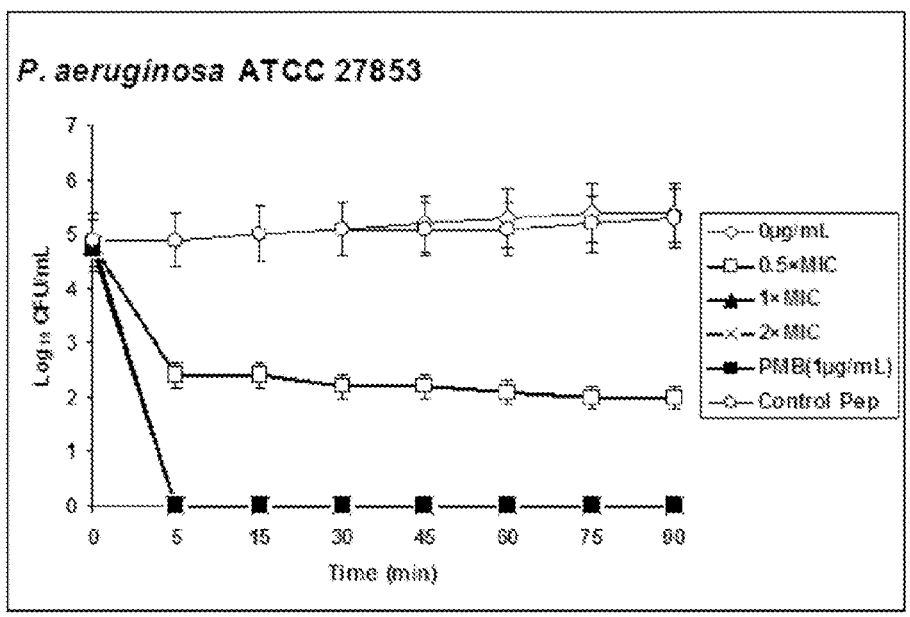

As EC5 demonstrated features common to an anti-microbial peptide, further experiments were carried out to investigate whether EC5 could exert anti-microbial effect in vitro. Mid-logarithmic phase cultures of bacteria with an inoculum of $10^5$ CFU/ml were incubated with peptide concentrations ranging from 0 to 50 µg/ml in a shaker incubator for 2 h following which the samples were plated on NA agar plates and CFU determined. EC5 showed a reduction of 5 $\log_{10}$ CFU/ml of *E. coli* and *P. aeruginosa* at peptide concentrations of 12.5, 25 and 50 µg/ml as observed by absence of colonies on NA plates (FIG. 3). However it showed no activity against any of the other bacteria tested even at 50 µg/ml.

Minimal inhibitory concentration (MIC) of EC5 was determined for the reference strains (Table 3). EC5 was highly active against *E. coli* ATCC 700928 and ATCC 25922 with a MIC of 8 µg/ml. *P. aeruginosa* ATCC 27853 growth was inhibited at a MIC of 8 µg/ml and *P. aeruginosa* ATCC 12121 with a MIC range of 16-32 µg/ml. MIC of EC5 against *K pneumoniae* was shown to be at 64-128 µg/ml. Minimum Bactericidal Concentration (MBC) of EC5 against *E. coli* ATCC 700928, ATCC 25922 and *P. aeruginosa* ATCC 27853 was 8 µg/ml, indicating that EC5 is bactericidal. However EC5 was not active against *S. aureus, S. epidermidis,* and *B. cereus*, indicating that it is specific.

Time-kill kinetic studies of EC5 was comparable to polymyxin B and exhibited most rapid bactericidal activity against *E. coli* ATCC (700928; 25922) and *P. aeruginosa* ATCC (12121; 27853) (FIG. 4) with complete inhibition after 5 min incubation with the peptide and showed no regrowth until 24 hrs. EC5 showed bactericidal activity in a dose-dependent manner. MBC concentration of 8 µg/ml showed complete killing of *E. coli* while growth inhibitory concentration of 4 µg/ml showed reduction of 2-3 $\log_{10}$ CFU/ml at around 45 min of exposure to the peptide. Control peptide with no anti-microbial activity was used as negative control.

Example 6

Figure 5A:
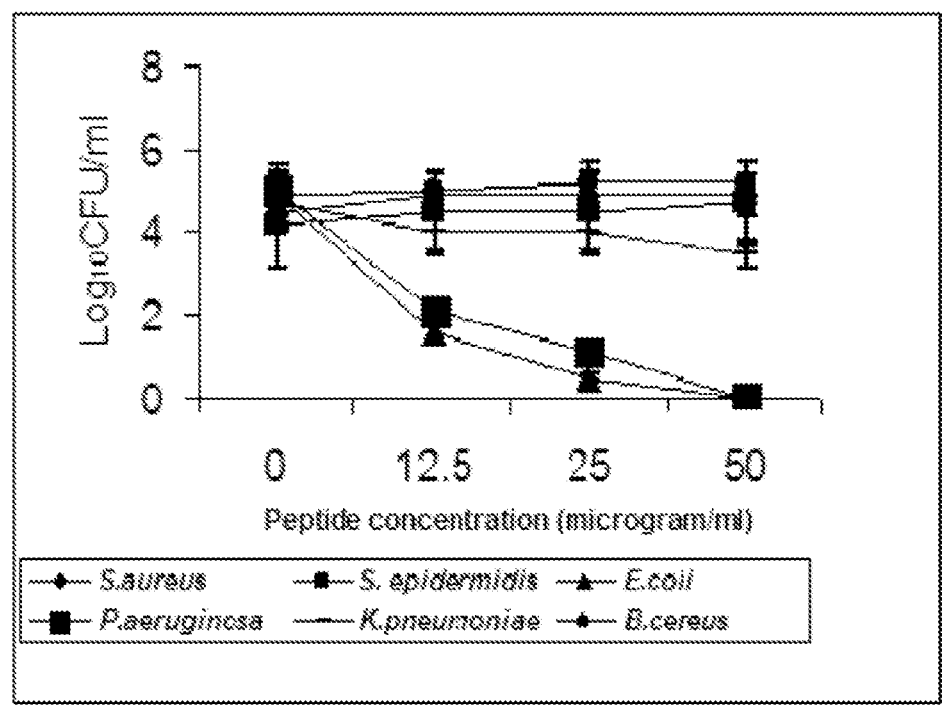
FIGS. 5A-5B. Effect of EC5 on different bacteria. A. Plasma, B. Platelets. Blood matrices were spiked with bacteria and incubated with different concentrations of EC5. Growth was monitored after 2 h by plating them onto Nutrient Agar (NA) plates.

EC5 Demonstrates Bactericidal Activity in the Presence of Plasma and Platelets Peptides that exhibit anti-microbial activity in conventional media may lose activity in biological media. EC5 was tested for its bactericidal activity in platelet and plasma samples spiked with the test bacteria as mentioned in materials and methods. The results illustrated in FIG. 5A suggest that EC5 was able to bring around 5 $\log_{10}$ CFU/ml reduction of *E. coli* and *P. aeruginosa* in plasma at 50 µg/ml. *E. coli* showed 4.5 and 3.5 $\log_{10}$ reduction at 25 and 12.5 µg/ml and *P. aeruginosa* showed around 4 and 3-$\log_{10}$ CFU/ml reduction at 25 and 12.5 µg/ml respectively. *K pneumoniae* showed around 2.5-$\log_{10}$ reduction in plasma when EC5 was at 50 µg/ml and around 1.5-$\log_{10}$ reduction at 25 µg/ml. However EC5 failed to cause a significant reduction in *S. aureus, S. epidermidis* and *B. cereus* even at 50 µg/ml.

Figure 5B:
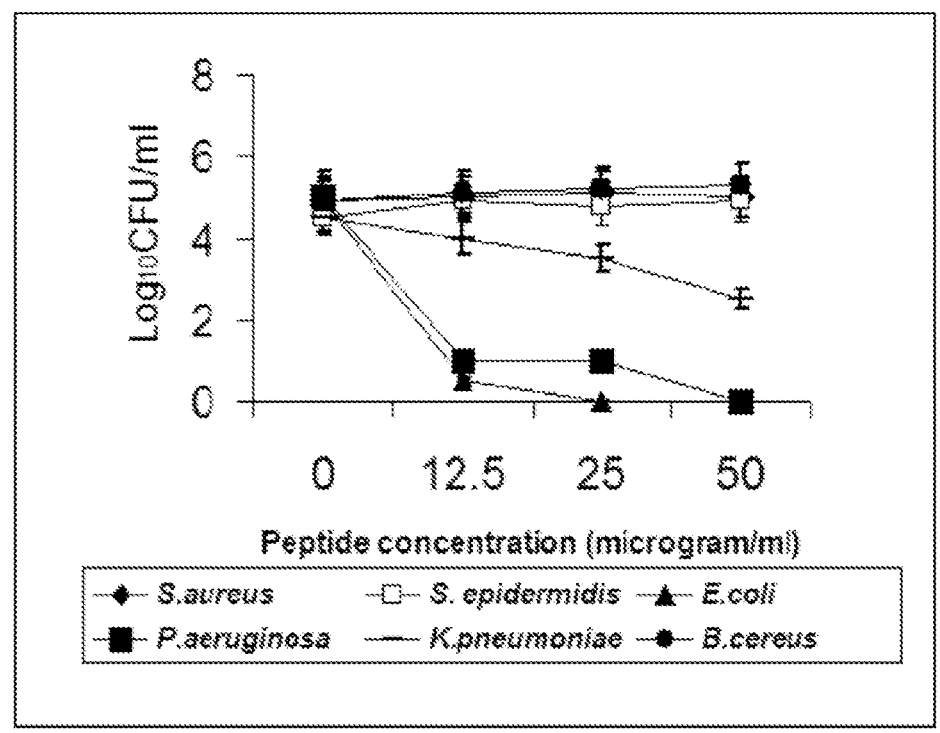
Figure 6:
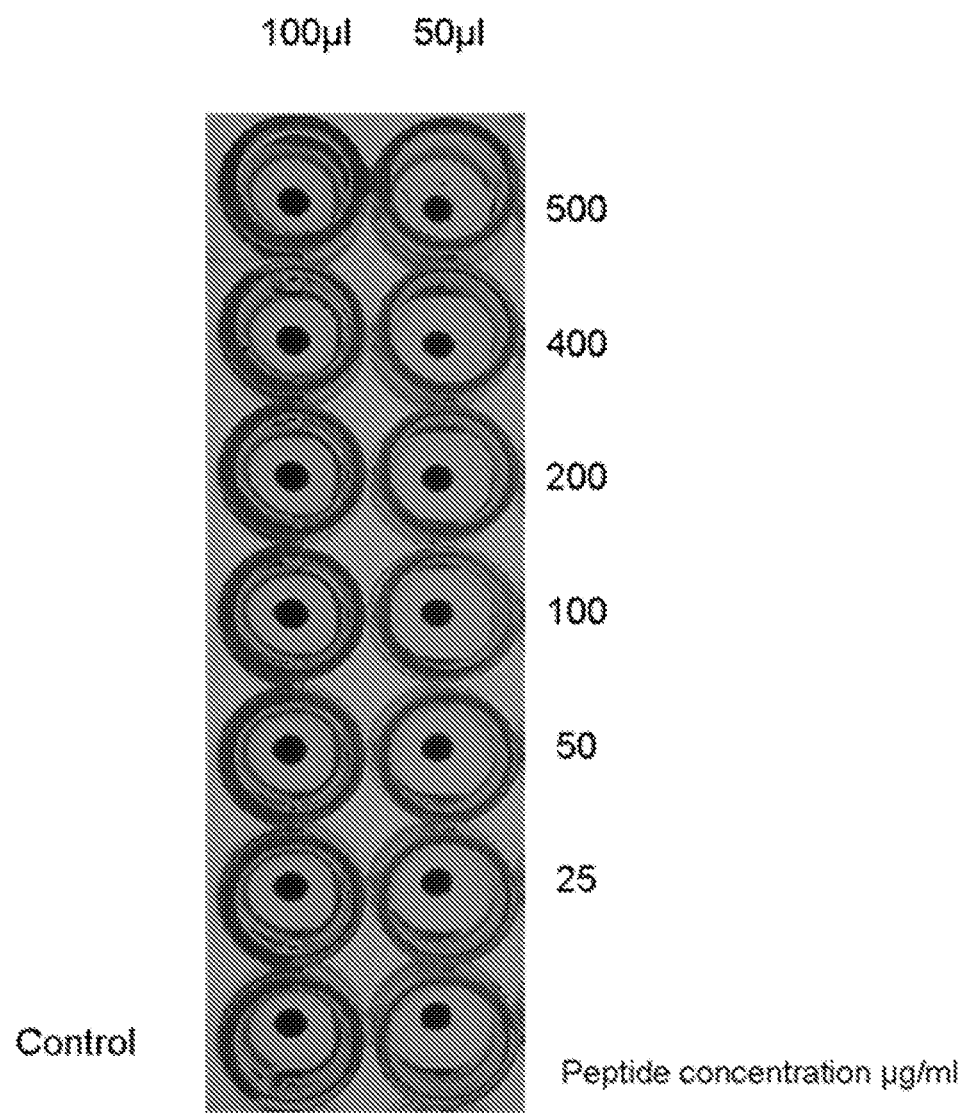
FIG. 6. Hemolytic activity of EC5. One percent suspensions of chicken RBCs were made with PBS. 100 μl and 50 μl of this suspension were incubated with different concentrations of the peptide in 96 well microtiter plates. Results were read visually.

EC5 at 50 and 25 µg/ml concentration in platelets showed no detectable *E. coli* colonies, while 12.5 µg/ml caused a reduction of 4.5 $\log_{10}$ CFU/ml compared to controls (FIG. 5B). *P. aeruginosa* also showed dose-dependent efficacy in platelets with reduction of 4 $\log_{10}$ CFU/ml in the presence of EC5 at 25 and 12.5 µg/ml, respectively. *K pneumoniae* showed reduction of 2.5, 1.5 and 1 $\log_{10}$CFU/m at EC5 of 50, 25, 12.5 µg/ml, respectively. No significant reduction was seen with *S. aureus, S. epidermidis* and *B. cereus* even at high concentrations.

Figure 7:
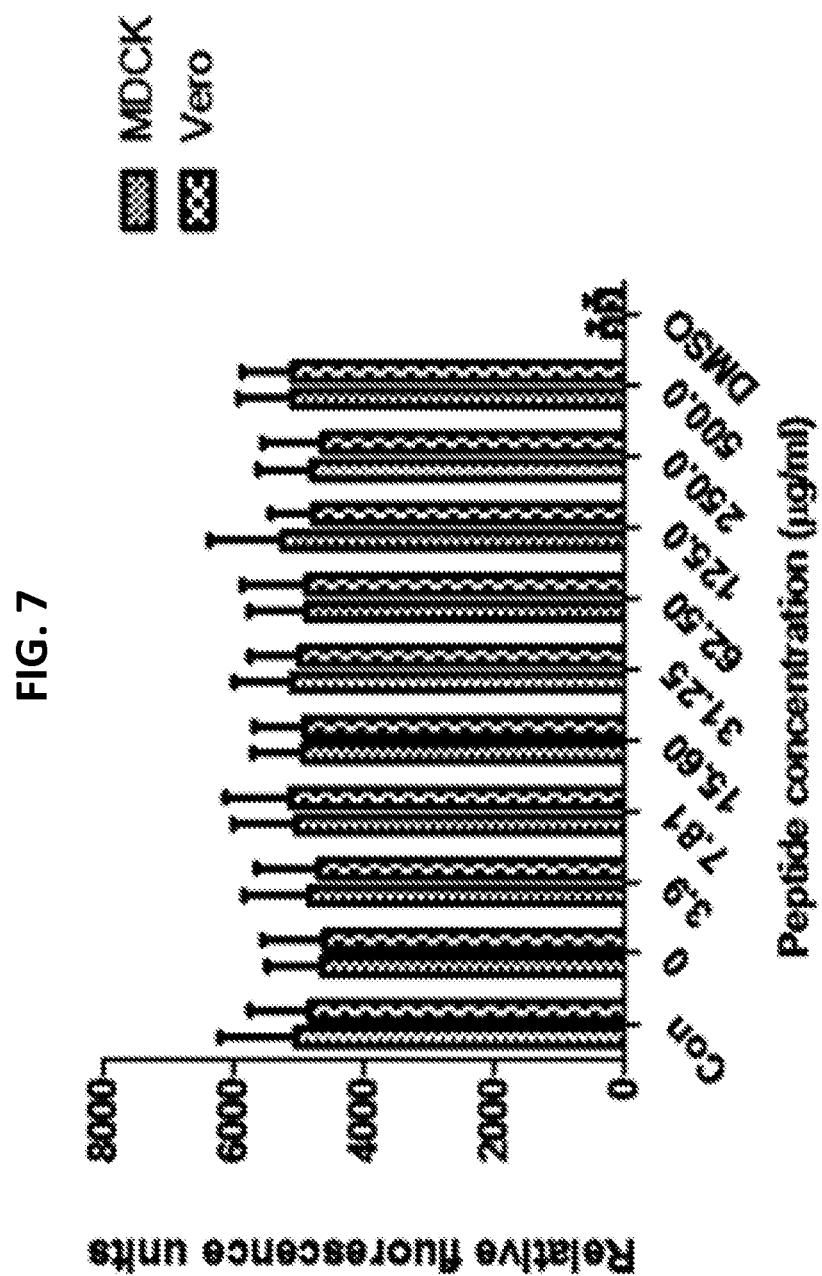
FIG. 7. Cytotoxicity of the peptides. MDCK and Vero cells were used to evaluate the toxicity of the peptide EC5 to mammalian cells.
Figure 8A:
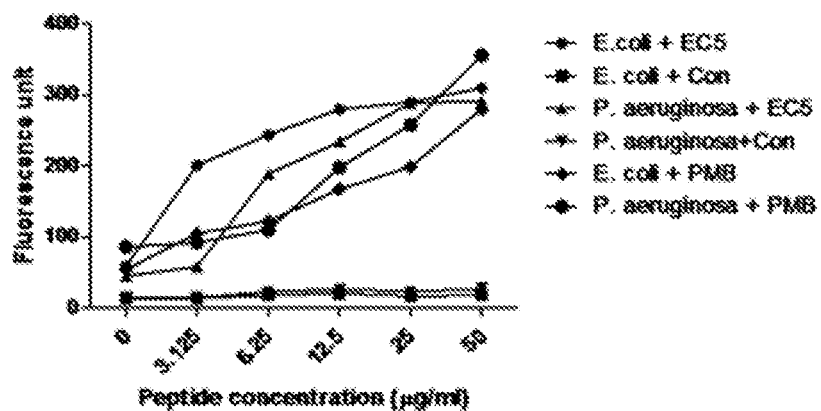
FIGS. 8A-8D. Mechanism of action of EC5 against E. coli and P. aeruginosa. A. Outer-membrane permeabilization mediated by EC5 as assessed by 1-N-phenylnaphthylamine (NPN) uptake. Effects of EC5 and Polymyxin B on NPN fluorescence. Value on y axis is the maximum fluorescence upon NPN uptake by the bacteria. B. EC5-induced permeability of bacterial cells studied using Syto9 and PI staining. Peptide-treated cells had increased membrane permeability as seen by increase in red fluorescence whereas live or untreated cells showed increase in green fluorescence. C. Cytoplasmic membrane depolarization using the fluorescent dye $diSC_3$-5. Corresponding values on y axis represents maximum intensity upon release of the dye mediated by EC5 plotted against time (min). D. EC5 mediated inhibition of ATP synthesis. ATP concentration was measured after the addition of EC5 and polymyxin B at various concentrations and the luminescence units measured.
Figure 8B:
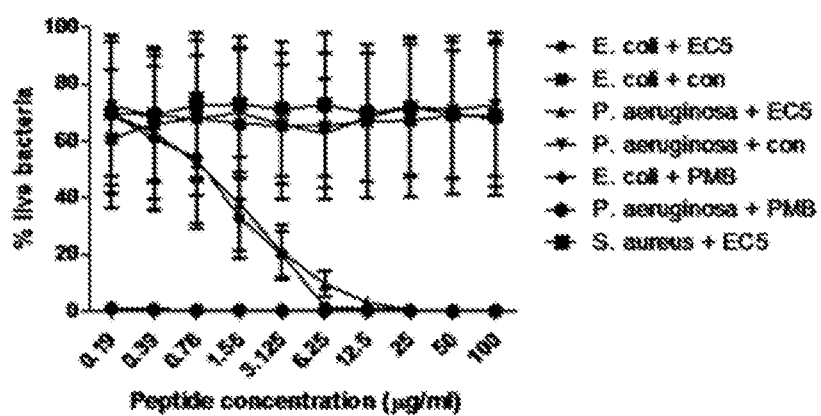
Figure 8C:
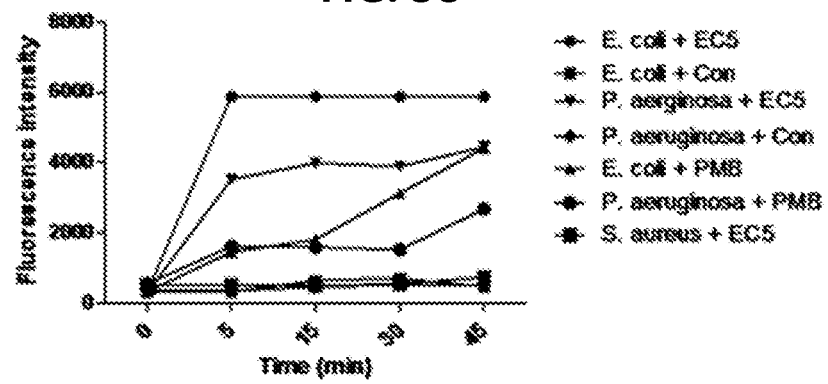
Figure 8D:
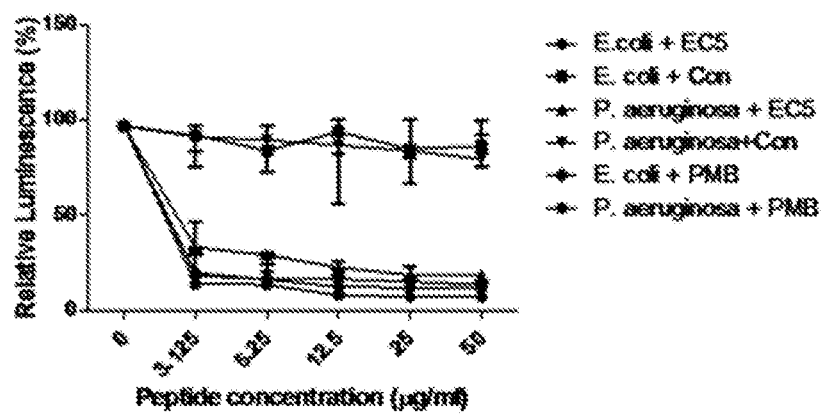

AMPs that kill bacteria may also exhibit hemolytic activity. The hemolytic activity of EC5 against chRBCs was determined as a measure of peptide toxicity toward higher eukaryotic cells (Yount, N. Y., et al., (2011) *PLoS. One.* 6, e26727; Tachi, T., et al., *Biochemistry* 41, 10723-10731). MHC is the maximal peptide concentration that produces no hemolysis after 24 h of incubation at 37° C. EC5 showed non-hemolytic activity against chRBCs at a concentration of up to 500 µg/ml (FIG. 7).

Example 7

Lack of Cytotoxicity

AMPs have gained attention over the recent years. However issues such as cytotoxicity have limited their use. The toxicity of the peptide to MDCK cells and Vero cells was tested by PRESTOBLUE™ Cell Viability assay (FIG. 8). All tested concentrations of EC5 up to 500 µg/ml showed no cytotoxicity against MDCK and Vero cells.

Example 8

Mechanism of Action of EC5

Outer Membrane Depolarization

Figure 9:
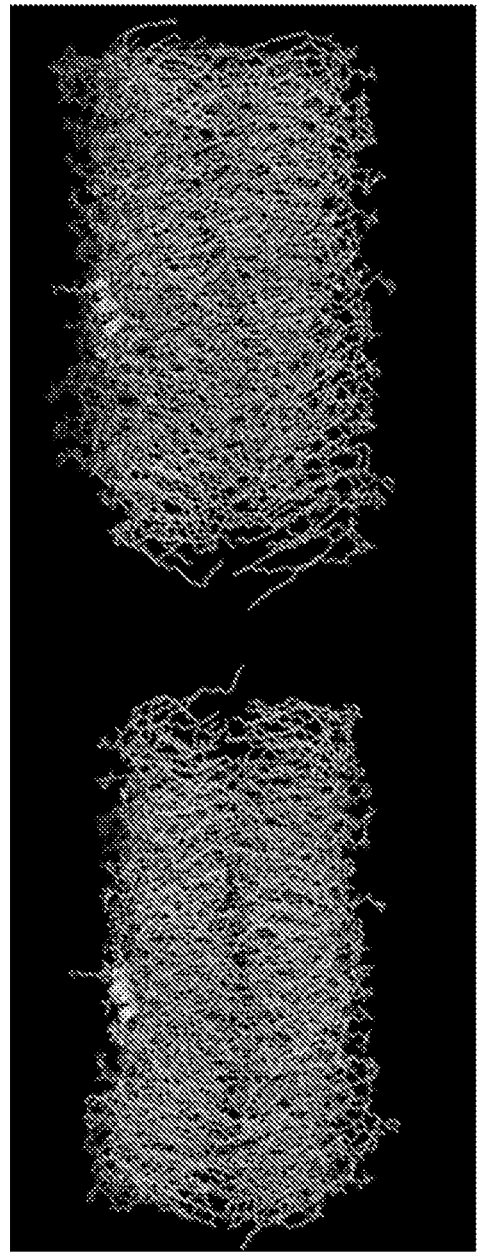
FIG. 9. Anti-Microbial Peptide (AMP)-bacterial membrane interaction studied by molecular dynamic simulations. EC5 was simulated with a POPE (1-palmitoyl-2-oleoyl-phosphaethanolamine) membrane bilayer model using the Cluspro 2.0 and Hex protein docking server. Program Data Base (PDB) files generated were visualized using PYMOLv0.99.

Outer membrane permeabilizing activity of EC5 against *E. coli* and *P. aeruginosa* was determined using the fluorescent dye N-phenyl-1-napthylamine (NPN) assay. The outer membrane of a bacterial cell is impermeable to NPN under normal conditions. However permeabilization of outer membrane by anti-microbial peptides allows the uptake of NPN thereby leading to increase in fluorescence in the cell. FIG. 9A shows dose-dependent increase in fluorescence in the presence of NPN in *E. coli* and *P. aeruginosa*, indicating that the peptide EC5 was able to disrupt the outer membrane of *E. coli* and *P. aeruginosa*. The outer membrane permeabilizing activity of EC5 was compared to polymyxin B, a well studied membrane permeabilising agent (Daugelavicius, R., et al., (2000) *Antimicrob. Agents Chemother.* 44, 2969-2978). When both *E. coli* and *P. aeruginosa* were incubated with EC5, an increase in fluorescence was observed that was higher than for polymyxin B at similar concentrations.

Cytoplasmic Membrane Permeabilization Assay

The membrane permeabilizing activity of EC5 was also studied using the SYTO9 and PI staining method. SYTO9 stain labels both live and dead bacteria when alone, but propidium iodide stains only cells with damaged membranes, reducing the level of green fluorescent SYTO9 when both the dyes are present. Hence the live cells appear green and the membrane damaged or dead cells appear red. The ratio of green versus red fluorescence can be calculated as a measure of live bacteria. FIG. 9B shows that EC5 exhibited concentration-dependent activity against *E. coli* and *P. aeruginosa*. Polymyxin B, an AMP with a net charge of +5 with membrane permeabilizing activity was used as positive control. Comparison of PI and SYTO9 fluorescence showed that polymyxin B was able to permeabilize almost all bacterial cell membranes even at the lowest concentration used. EC5 at 6.25 µg/ml and 12.5 µg/ml showed maximum permeability of *E. coli* and *P. aeruginosa* cells respectively.

Membrane Depolarization

Cytoplasmic depolarization assay($\Delta\psi$) was performed using the membrane potential sensitive dye 3,3'-dipropylthiadicarbocyanine iodide (diSC$_3$-5) (Zang, L. et al., (2001) *J. Biol. Chem.* 276, 35714-35722). This dye can cross the outer membrane of the bacterial cell and become concentrated in the cytoplasmic membrane and thereby it self-quenches its own fluorescence. Upon addition of a membrane-permeabilizing agent the dye is released with consequent increase in the fluorescence. EC5 at 8 µg/ml and 16 µg/ml caused rapid depolarization of the cytoplasmic membrane in both *E. coli* and *P. aeruginosa* resulting in the release of diSC$_3$-5 within 5 min (FIG. 9C). The killing was also rapid, resulting in complete inhibition of CFU within 5 min of exposure of the peptide. However Polymyxin B even at its MIC of 0.5 µg/ml caused slow release of diSC$_3$-5 when compared to EC5. *S. aureus* with EC5 showed no trace of release of diSC$_3$-5 even after 45 min at 64 µg/ml.

ATP Inhibition by EC5

ATP inhibition as a measurement of microbial viability was measured using BacTiter-Glo kit (Invitrogen, USA). Intracellular ATP levels of *E. coli* and *P. aeruginosa* were examined after the addition of different concentrations of EC5 (FIG. 9D). ATP inhibition began 5 min after the addition of EC5 at lowest concentration of 3.125 µg/ml which was slightly lower than the MIC of 8 µg/ml for *E. coli* and *P. aeruginosa*. The level of ATP did not rise after the addition of EC5. These results suggest that EC5 disrupts the cytoplasmic membrane thereby resulting in reduced ATP levels, leading to cell death.

Molecular Dynamics-In-silico studies of EC-5 lipid interactions were performed by Cluspro 2.0 and Hex protein docking server. EC5 was docked onto the polar head group of POPE lipid bilayer. 3D model structures were visualized using PYMOLv0.99. Docking studies showed that EC5 was adsorbed onto the surface of the lipid bilayers by adopting an orientation parallel to the lipid surface and thereby causing a disruption of the lipid headgroup packing (FIG. 10). EC5 also showed penetration into the lipid bilayers suggesting the degree of peptide interaction with POPE.

Example 9

Additional Peptides

In this study a whole-cell phage-display approach was used to identify peptides binding to the cell surface of *E. coli*. By using this approach, a specific sequence, represented by EC5 (RLLFRKIRRLKR), was identified that repeated multiple times (5 out of 10 clones). Interestingly the aligned sequences contained conserved Arginine (R) and Lysine (L) residues. These Arginine and Lysine residues have been shown to be major components of anti-microbial peptides (Chen, P., et al., (2003) *Am. J. Vet. Res.* 64, 1088-1092). The majority of native anti-microbial peptides have net charge ranging from +2 to +8 and hydrophobic value ranging from 41% to 50% (Jiang, Z., et al., (2008) *Chem. Biol. Drug Des* 72, 483-495; Jiang, Z., et al., (2008) *Biopolymers* 90, 369-383; Jiang, Z., et al., (2009) *Adv. Exp. Med. Biol.* 611, 561-562). EC5 showed features common to anti-microbial peptides: net positive charge of +7 and hydrophobic value of 41%. Sequence analysis of EC5 suggested that it was a cationic α-helical peptide.

EC5 showed anti-microbial properties deemed bactericidal by structure analysis of the peptide and hence the bactericidal activity of the peptide was investigated in vitro. The best bactericidal AMP kills bacteria in vitro, including certain antibiotic-resistant pathogens, with MICs ranging from 1 to 8 µg/ml (Hancock, R. E. (1997) *Lancet* 349, 418-422). EC5 is a narrow spectrum anti-bacterial agent and was most effective against Gram-negative bacteria tested, with an MIC of 8 µg/ml for *E. coli* strains and a MBC of 8 µg/ml. *P. aeruginosa* had an MIC of 8 µg/ml for ATCC 27853 and 16-32 µg/ml for *P. aeruginosa* ATCC 12121. The peptide EC5 showed no activity against Gram-positive strains and appeared to be more active against Gram-negative strains with a MIC of 4-128 µg/ml.

While AMPs are effective in vitro, they may lose their activity in vivo, when given intravenous since human blood may have factors such as proteins or small nucleic acids that can adsorb AMPs and hinder their activity. In this study an ex vivo assay using human plasma and platelets as the test medium was developed to evaluate the extent and duration of EC5 efficacy. The EC5 peptide was introduced simultaneously along with the test organisms into the medium and incubated for 2 h. In this experimental setup, EC5 exhibited potent bactericidal activity in homologous plasma and inhibited E. coli and P. aeruginosa at concentration of 50 μg/ml.

However, at lower concentration the peptide did not retain the similar effect as in conventional media. EC5 in the presence of platelets suspended in plasma showed complete inhibition of E. coli at 25 and 50 μg/ml. However at 12.5 μg/ml, it showed only 4.5 $\log_{10}$ reduction in CFU/ml. Also, the activity of EC5 was lower against P. aeruginosa in the presence of platelets suspended in plasma compared to what is observed in conventional media. These observations suggest that some plasma factors could interfere with, or masking the effect of EC5, but only at lower concentrations.

The non-hemolysis of chRBCs even at a concentration of 500 μg/ml and non-cytotoxicity of the peptide after prolonged incubation makes EC5 an ideal drug candidate. Since the peptide MIC and peptide concentrations inducing hemolysis differ by more than an order of magnitude, the data indicates that EC5 therapeutic index for the treatment of bacterial infections is favorable.

Many AMPs kill bacterial cells by disrupting their membrane integrity. The interaction of peptides with membranes using membrane permeabilization assays. EC5 caused rapid increase in outer membrane permeabilization at lower concentration, below MBC, which was followed by cytoplasmic depolarization. The changes correlated well with cell killing and cytoplasmic depolarization at the same time. However, polymyxin B at 3.125 μg/ml resulted in complete inhibition of CFU within 5 min of exposure of the peptide, but only minimal release of $diSC_35$ from the cells after 5 min of exposure. Polymyxin B causes cell death prior to cytoplasmic depolarization whereas for EC5 both the events appear to occur at the same time. These observations suggest that EC5 may disrupt the cytoplasmic membrane, causing rapid depolarization, and inhibition of macromolecular synthesis as seen by ATP inhibition and rapid cell death. In order to confirm this hypothesis, the peptide-membrane interaction was investigated using molecular dynamic simulations. EC5 was simulated with POPE/POPG membrane bilayer model using the Hex docking server (hexserver.loria.fr/) and Cluspro protein-protein docking server (Version 2.0). Docking results suggested that EC5 may lie parallel to the membrane and translocate across the cytoplasmic membrane. These results suggest that EC5 penetrates bacterial-mimicking membranes as a result of electrostatic interactions which are essential for peptides to interact with membrane surface. The peptide then integrates into the cell membrane, causing depolarization and cell death (Shepherd, C. M., et al., (2001) Biophys. J. 80, 579-596). Currently Gram-negative bacteria such as E. coli and P. aeruginosa are causing concern due to the rapid spread of extremely resistant strains to traditional antibiotics.

The use of polymyxin B was abandoned previously since the antibiotic showed high toxicity, especially nephrotoxicity (Falagas, M. E. and Kasiakou, S. K. (2005) Clin. Infect. Dis. 40, 1333-1341; Vaara, M., et al., (2008) Antimicrob. Agents Chemother. 52, 3229-3236; Velkov, T. et al., (2010) J. Med. Chem. 53, 1898-1916). EC5 showed potent in vitro and low cytotoxicity, demonstrating their use as promising candidate for the development of new anti-bacterial drugs. Since EC5 shows membrane-permeabilizing properties it can also be used in combination with conventional antibiotics to facilitate the entry of drugs into the cells. Combination therapy with antibiotics can potentially be used to broaden the anti-microbial spectrum to treat multiple-drug resistant strains (Rishi, P., et al., (2011) Antimicrob. Agents Chemother. 55, 4176-4182).

The following additional peptides were designed based on the EC5 structure:

TABLE 2

Peptides with similar anti-microbial potential

| | Amino Acid Sequence | SEQ ID NO: | Comparison to EC5 |
|---|---|---|---|
| 1 | RLLFRKIRRLKR | SEQ ID NO: 1, wherein $X_1$ is R; $X_2$ is L; $X_3$ is R; $X_4$ is K; $X_5$ is I; $X_6$ is R; $X_7$ is R; $X_8$ is L; and $X_9$ is K and $X_{10}$ is R | EC5 |
| 2 | WLLFRKIRRLKW | SEQ ID NO: 1, wherein $X_1$ is W; $X_2$ is L; $X_3$ is R; $X_4$ is K; $X_5$ is I; $X_6$ is R; $X_7$ is R; $X_8$ is L; and $X_9$ is K and $X_{10}$ is W | R,P,C |
| 3 | RLARLLFRKIRRLKR | SEQ ID NO: 2, wherein $X_1$ is R; $X_2$ is L; $X_3$ is R; $X_4$ is K; $X_5$ is I; $X_6$ is R; $X_7$ is R; $X_8$ is L; and $X_9$ is K and $X_{10}$ is R, $X_{11}$ is R, $X_{12}$ is L; $X_{13}$ is A; and $X_{14}$, $X_{15}$ and $X_{16}$ are no amino acid | R,C,A,W |
| 4 | RLLFRKIRRLKRCAW | SEQ ID NO: 2, wherein $X_1$ is R; $X_2$ is L; $X_3$ is R; $X_4$ is K; $X_5$ is I; $X_6$ is R; $X_7$ is R; $X_8$ is L; and $X_9$ is K and $X_{10}$ is R, $X_{11}$, $X_{12}$ and $X_{13}$ are no amino acid; $X_{14}$ is C; $X_{15}$ is A and $X_{16}$ is W | R,C,A,W |
| 5 | RCLFRKIRRLKR | SEQ DI NO: 1, wherein $X_1$ is R; $X_2$ is C; $X_3$ is R; $X_4$ is K; $X_5$ is I; $X_6$ is R; $X_7$ is R; $X_8$ is L; and $X_9$ is K and $X_{10}$ is R | C |
| 8 | R-LFRKI-RL-R | SEQ ID NO: 1 wherein $X_1$ is R, $X_2$ no amino acid; $X_3$ is R; $X_4$ is K; $X_5$ is I; $X_6$ is no amino acid; $X_7$ is R; $X_8$ is L; $X_9$ is no amino acid; and $X_{10}$ is R | Delete L,R,K |
| 12 | RLLF-KIR--KR | SEQ ID NO: 1, wherein $X_1$ is R, $X_2$ is L; $X_3$ is no amino acid; $X_4$ is K; $X_5$ is I; $X_6$ is R; $X_7$ is no amino acid; $X_8$ is no amino acid; $X_9$ is K; and $X_{10}$ is R | Delete R,R,L |
| 14 | RLLF---RRLKR | SEQ ID NO: 1 wherein $X_1$ is R, $X_2$ is L; $X_3$ is no amino acid; $X_4$ is no amino acid ; $X_5$ is no amino acid ; $X_6$ is R; $X_7$ is R; $X_8$ is L; $X_9$ is K; and $X_{10}$ is R | Delete R,K,I |
| 15 | RLLFR---RLKR | SEQ ID NO: 1, wherein $X_1$ is R, $X_2$ is L; $X_3$ is R; $X_4$ is no amino acid; $X_5$ is no amino acid; $X_6$ is no amino acid; $X_7$ is R; $X_8$ is L; $X_9$ is K; and $X_{10}$ is R | Delete K,I,R |

In conclusion, these studies demonstrate that peptides with anti-microbial activity can be selected from random phage libraries and may prove useful in the development of novel bactericidal agents.

In view of the many possible embodiments to which the principles of our invention may be applied, it should be recognized that illustrated embodiments are only examples of the invention and should not be considered a limitation on the scope of the invention. Rather, the scope of the invention is defined by the following claims. We therefore claim as our invention all that comes within the scope and spirit of these claims.

We claim:

1. An isolated peptide of 9 to 15 amino acids in length, comprising the amino acid sequence set forth as
$X_1X_2LFX_3X_4X_5X_6X_7X_8X_9X_{10}$ (SEQ ID NO: 1)
wherein $X_1$ is R or W, $X_2$ is L, C or no amino acid; $X_3$ is R or no amino acid; $X_4$ is K, C or no amino acid; $X_5$ is I or no amino acid; $X_6$ is R or no amino acid; $X_7$ is R, C or no amino acid; $X_8$ is L or no amino acid; $X_9$ is K or no amino acid; and $X_{10}$ is R or W, and wherein the peptide has a hydrophobicity score of 40-60%, a net charge of +5 to +7, and has anti-microbial activity against *E. coli* and *P. aeruginosa*,
and wherein the peptide comprises the amino acid sequence set forth as:
$X_{11}X_{12}X_{13}X_1X_2LFX_3X_4X_5X_6X_7X_8X_9X_{10}X_{14}X_{15}W$ (SEQ ID NO: 2)
wherein the N-terminal amino acid is an R; wherein $X_{11}$ is R or no amino acid; $X_{12}$ is R,C,A, or W; $X_{13}$ is R,C,A, or W; $X_{14}$, is C,A, or W and $X_{15}$ C,A,W or no amino acid.

2. An isolated peptide of 9 to 15 amino acids in length, comprising the amino acid sequence set forth as
$X_1X_2LFX_3X_4X_5X_6X_7X_8X_9X_{10}$ (SEQ ID NO: 1)
wherein $X_1$ is R or W, $X_2$ is L, C or no amino acid; $X_3$ is R or no amino acid; $X_4$ is K, C or no amino acid; $X_5$ is I or no amino acid; $X_6$ is R or no amino acid; $X_7$ is R, C or no amino acid; $X_8$ is L or no amino acid; $X_9$ is K or no amino acid; and $X_{10}$ is R or W, and wherein the peptide has a hydrophobicity score of 40-60%, a net charge of +5 to +7, and has anti-microbial activity against *E. coli* and *P. aeruginosa*,
and wherein the peptide comprises the amino acid sequence set forth as:
$X_1LLFRKIRRLKX_{10}$
(SEQ ID NO: 1, wherein $X_2$ is L; $X_3$ is R or no amino acid; $X_4$ is K; $X_5$ is I; $X_6$ is R; $X_7$ is R; $X_8$ is L; and $X_9$ is K);
and wherein $X_1$ is R or W and $X_{10}$ is R or W.

3. The isolated peptide of claim 2, wherein $X_1$ is R and $X_{10}$ is R or W.

4. The isolated peptide of claim 2, wherein $X_1$ is R or W and $X_{10}$ is R.

5. The isolated peptide of claim 4, comprising the amino acid sequence set forth as one of:
a) RLLFRKIRRLKR (SEQ ID NO: 1, wherein $X_1$ is R; $X_2$ is L; $X_3$ is R; $X_4$ is K; $X_5$ is I; $X_6$ is R; $X_7$ is R; $X_8$ is L; and $X_9$ is K and $X_{10}$ is R);
b) WLLFRKIRRLKW (SEQ ID NO: 1, wherein $X_1$ is W; $X_2$ is L; $X_3$ is R; $X_4$ is K; $X_5$ is I; $X_6$ is R; $X_7$ is R; $X_8$ is L; and $X_9$ is K and $X_{10}$ is W);

c) RLARLLFRKIRRLKR (SEQ ID NO: 2, wherein $X_1$ is R; $X_2$ is L; $X_3$ is R; $X_4$ is K; $X_5$ is I; $X_6$ is R; $X_7$ is R; $X_8$ is L; and $X_9$ is K and $X_{10}$ is R, $X_{11}$ is R, $X_{12}$ is L; $X_{13}$ is A; and $X_{14}$, $X_{15}$ and $X_{16}$ are no amino acid);

d) RLLFRKIRRLKRCAW (SEQ ID NO: 2, wherein $X_1$ is R; $X_2$ is L; $X_3$ is R; $X_4$ is K; $X_5$ is I; $X_6$ is R; $X_7$ is R; $X_8$ is L; and $X_9$ is K and $X_{10}$ is R, $X_{11}$, $X_{12}$ and $X_{13}$ are no amino acid; and $X_{14}$ is C; $X_{15}$ is A and $X_{16}$ is W); or e) RCLFRKIRRLKR (SEQ ID NO: 1, wherein $X_1$ is R; $X_2$ is C; $X_3$ is R; $X_4$ is K; $X_5$ is I; $X_6$ is R; $X_7$ is R; $X_8$ is L; and $X_9$ is K and $X_{10}$ is R).

6. The isolated peptide of claim 5, consisting of the amino acid sequence set forth as one of:

a) RLLFRKIRRLKR (SEQ ID NO: 1, wherein $X_1$ is R; $X_2$ is L; $X_3$ is R; $X_4$ is K; $X_5$ is I; $X_6$ is R; $X_7$ is R; $X_8$ is L; and $X_9$ is K and $X_{10}$ is R);

b) WLLFRKIRRLKW (SEQ ID NO: 1, wherein $X_1$ is W; $X_2$ is L; $X_3$ is R; $X_4$ is K; $X_5$ is I; $X_6$ is R; $X_7$ is R; $X_8$ is L; and $X_9$ is K and $X_{10}$ is W);

c) RLARLLFRKIRRLKR (SEQ ID NO: 2, wherein $X_1$ is R; $X_2$ is L; $X_3$ is R; $X_4$ is K; $X_5$ is I; $X_6$ is R; $X_7$ is R; $X_8$ is L; and $X_9$ is K and $X_{10}$ is R, $X_{11}$ is R, $X_{12}$ is L; $X_{13}$ is A; and $X_{14}$, $X_{15}$ and $X_{16}$ are no amino acid);

d) RLLFRKIRRLKRCAW (SEQ ID NO: 2, wherein $X_1$ is R; $X_2$ is L; $X_3$ is R; $X_4$ is K; $X_5$ is I; $X_6$ is R; $X_7$ is R; $X_8$ is L; and $X_9$ is K and $X_{10}$ is R, $X_{11}$, $X_{12}$ and $X_{13}$ are no amino acid; and $X_{14}$ is C; $X_{15}$ is A and $X_{16}$ is W); or e) RCLFRKIRRLKR (SEQ DI NO: 1, wherein $X_1$ is R; $X_2$ is C; $X_3$ is R; $X_4$ is K; $X_5$ is I; $X_6$ is R; $X_7$ is R; $X_8$ is L; and $X_9$ is K and $X_{10}$ is R).

7. The isolated peptide of claim 1, wherein the peptide is nine or twelve amino acids in length.

8. The isolated peptide of claim 1, comprising the amino acid sequence set forth as:

a) RLFRKIRLR (SEQ ID NO: 1 wherein $X_1$ is R, $X_2$ is no amino acid; $X_3$ is R; $X_4$ is K; $X_5$ is I; $X_6$ is no amino acid; $X_7$ is R; $X_8$ is L; $X_9$ is no amino acid; and $X_{10}$ is R);

b) RLLFKIRKR (SEQ ID NO: 1, wherein $X_1$ is R, $X_2$ is L; $X_3$ is no amino acid; $X_4$ is K; $X_5$ is I; $X_6$ is R; $X_7$ is no amino acid; $X_8$ is no amino acid; $X_9$ is K; and $X_{10}$ is R);

c) RLLFRRLKR (SEQ ID NO: 1, wherein $X_1$ is R, $X_2$ is L; $X_3$ is no amino acid; $X_4$ is no amino acid; $X_5$ is no amino acid; $X_6$ is R; $X_7$ is R; $X_8$ is L; $X_9$ is K; and $X_{10}$ is W); or d) RLLFRRLKR (SEQ ID NO: 1, wherein $X_1$ is R, $X_2$ is L; $X_3$ is R; $X_4$ is no amino acid; $X_5$ is no amino acid; $X_6$ is no amino acid; $X_7$ is R; $X_8$ is L; $X_9$ is K; and $X_{10}$ is R or W.

9. The isolated peptide of claim 8, consisting of the amino acid sequence set forth as one of:

a) RLFRKIRLR (SEQ ID NO: 1 wherein $X_1$ is R, $X_2$ no amino acid; $X_3$ is R; $X_4$ is K; $X_5$ is I; $X_6$ is no amino acid; $X_7$ is R; $X_8$ is L; $X_9$ is no amino acid; and $X_{10}$ is R);

b) RLLFKIRKR (SEQ ID NO: 1, wherein $X_1$ is R, $X_2$ is L; $X_3$ is no amino acid; $X_4$ is K; $X_5$ is I; $X_6$ is R; $X_7$ is no amino acid; $X_8$ is no amino acid; $X_9$ is K; and $X_{10}$ is R);

c) RLLFRRLKR (SEQ ID NO: 1, wherein $X_1$ is R, $X_2$ is L; $X_3$ is no amino acid; $X_4$ is no amino acid; $X_5$ is no amino acid; $X_6$ is R; $X_7$ is R; $X_8$ is L; $X_9$ is K; and $X_{10}$ is W); or d) RLLFRRLKR (SEQ ID NO: 1, wherein $X_1$ is R, $X_2$ is L; $X_3$ is R; $X_4$ is no amino acid; $X_5$ is no amino acid; $X_6$ is no amino acid; $X_7$ is R; $X_8$ is L; $X_9$ is K; and $X_{10}$ is R or W.

10. The isolated peptide of claim 6, consisting of the amino acid sequence set forth as RLLFRKIRRLKR (SEQ ID NO: 1, wherein $X_1$ is R; $X_2$ is L; $X_3$ is R; $X_4$ is K; $X_5$ is I; $X_6$ is R; $X_7$ is R; $X_8$ is L; and $X_9$ is K and $X_{10}$ is R).

* * * * *